US005512464A

United States Patent [19]

Spencer et al.

[11] Patent Number: 5,512,464
[45] Date of Patent: Apr. 30, 1996

[54] METHOD OF PRODUCING HIGH FRUCTOSE CORN SYRUP FROM GLUCOSE USING NOBLE GASES

[75] Inventors: Kevin C. Spencer, Riverside; Christine E. Boisrobert, Chicago; Steven A. Fisher, Berwyn; Patricia A. Rojak, Wheaton; Karen S. Sabatini, Summit, all of Ill.

[73] Assignee: American Air Liquide, New York, N.Y.

[21] Appl. No.: 270,224

[22] Filed: Jul. 1, 1994

Related U.S. Application Data

[63] Continuation of Ser. No. 816,732, Jan. 3, 1992, abandoned.

[51] Int. Cl.$^6$ ............................ C12P 19/24; C12P 19/02; C13K 11/00

[52] U.S. Cl. ................................ 435/94; 127/30; 127/42; 127/44; 426/658; 435/105; 435/234

[58] Field of Search ........................... 435/94, 234, 105; 127/29, 30, 42, 44; 426/658

[56] References Cited

U.S. PATENT DOCUMENTS

| | | |
|---|---|---|
| 2,569,217 | 9/1951 | Bagdigian . |
| 3,143,471 | 8/1964 | Coady . |
| 3,183,171 | 5/1965 | Schreiner . |
| 3,378,443 | 4/1968 | Cooper et al. . |
| 3,677,024 | 7/1872 | Segall . |
| 3,725,076 | 4/1973 | Stefanucci et al. . |
| 3,910,821 | 10/1975 | Cory ......................................... 435/94 |
| 3,957,892 | 5/1876 | Kleiman . |
| 4,008,754 | 2/1977 | Kraushaar et al. . |
| 4,017,363 | 4/1977 | McMullen et al. . |
| 4,044,004 | 8/1977 | Saucy et al. . |

(List continued on next page.)

FOREIGN PATENT DOCUMENTS

| | | |
|---|---|---|
| 989311 | 5/1876 | Canada . |
| 204532 | of 0000 | European Pat. Off. . |
| 0111595 | 6/1984 | European Pat. Off. . |
| 0346201 | 12/1989 | European Pat. Off. . |
| 0412155 | 2/1991 | European Pat. Off. . |
| 0440273 | 8/1991 | European Pat. Off. . |
| 2406567 | 5/1879 | France . |
| 1339669 | 9/1963 | France . |
| 1454653 | 8/1966 | France . |
| 2156559 | 6/1973 | France . |
| 2225095 | 11/1974 | France . |
| 2261518 | 9/1975 | France . |
| 2643232 | 8/1990 | France . |
| 0635601 | 9/1936 | Germany . |
| 3007712 | 10/1981 | Germany . |
| 52-27699 | 9/1972 | Japan . |
| 52-86987 | 7/1977 | Japan . |
| 52-97913 | 8/1977 | Japan . |
| 54-129185 | 10/1979 | Japan . |
| 1-059647 | 1/1980 | Japan . |
| 58-39650 | 3/1983 | Japan . |
| 58-107180 | 6/1983 | Japan . |
| 60-56984 | 4/1985 | Japan . |
| 63-77848 | 4/1988 | Japan . |
| 2-104502 | 4/1990 | Japan . |
| 3-200568 | 9/1991 | Japan . |
| 1289437 | 2/1987 | U.S.S.R. . |
| 0415656 | 8/1934 | United Kingdom . |
| 1376362 | 12/1974 | United Kingdom . |
| 2029846 | 3/1980 | United Kingdom . |
| 2091556 | 8/1982 | United Kingdom . |

OTHER PUBLICATIONS

Colton et al., *Undersea Biomed Res.*, vol. 17(4), 1990, pp. 297–304.
Chemical Abstracts, vol. 68, No. 14, AN–60751j.
Chemical Abstracts, vol. 74, No. 23, AN–121276I.
Chemical Abstracts, vol. 76, No. 13, AN–70898s.
Chemical Abstracts, vol. 80, No. 7, AN–35579z.
Chemical Abstracts, vol. 80, No. 11, AN–56112g.
Chemical Abstracts, vol. 86, No. 3, AN–14672h.
Chemical Abstracts, vol. 87, No. 22, AN–172800y.
Chemical Abstracts, vol. 91, No. 17, AN–138183x.
Chemical Abstracts, vol. 93, No. 24, AN–225670p.
Chemical Abstracts, vol. 97, No. 18, AN–145890c.
Chemical Abstracts, vol. 98, No. 10, AN–78191f.
Chemical Abstracts, vol. 99, No. 21, AN–172397v.
Chemical Abstracts, vol. 106, No. 25, AN–210601e.
Chemical Abstracts, vol. 115, No. 20, AN–214644e.
WPI Abstracts, AN–70–84762R, DE–1753586.
WPI Abstracts, AN–82–05785E, DE–3 202 622, Sep. 9, 1982.
Federation Proceedings, vol. 27, No. 3, May–Jun. 1968, H. R. Schreiner, "General Biological Effects of the Helium–Xenon Series of Elements".
156 Food Technology, vol. 34, No. 6, Jun. 1980, p. 102.
Federation Proceedings, vol. 26, No. 2, Mar.–Apr. 1967, p. 650, G. F. Doebbler, et al., "Inert Gas Interactions and Effects on Enzymatically Active Proteins".
Febs Letters, vol. 62, No. 3, Mar. 1976, pp. 284–287, K. Sandhoff, et al., "Effect of Xenon, Nitrous Oxide and Halothane on Membrane–Bound Sialidase from Calf Brain".
Aviation, Space and Environmental Medicine, vol. 48, No. 1, Jan. 1977, pp. 40–43, S. K. Hemrick, et al., "Effect of Increased Pressures of Oxygen, Nitrogen, and Helium on Activity of a Na–K–Mg ATPase Of Beef Brain".
Undersea Biomedical Research, vol. 17, No. 4, 1990, pp. 297–303, J. S. Colton, et al., "Effect of Helium and Heliox on Glutamate Decarboxylase Activity".
Sciences Des Aliments, vol. 4, No. 4, 1984, pp. 595–608, B. Pichard, et al., "Effect of Nitrogen, Carbon Monoxide and Carbon Dioxyde on the Activity of Proteases of Pseudomonas Fragi and Streptomyces Caespitosus".

*Primary Examiner*—Herbert J. Lilling
*Attorney, Agent, or Firm*—Oblon, Spivak, McClelland, Maier & Neustadt

[57] ABSTRACT

A process for producing high fructose corn syrup from glucose containing syrup, which entails isomerizing the glucose containing syrup through an enzymatic reaction to make high fructose corn syrup, wherein the enzymatic reaction occurs in a gas containing solution which comprises at least one gas selected from the group consisting of noble gas.

11 Claims, 17 Drawing Sheets

U.S. PATENT DOCUMENTS

| | | |
|---|---|---|
| 4,136,049 | 1/1979 | Horiishi et al. . |
| 4,138,565 | 2/1979 | Ehrhardt et al. . |
| 4,308,264 | 12/1981 | Conway et al. . |
| 4,314,810 | 2/1982 | Fourcadier et al. . |
| 4,315,266 | 2/1982 | Ellis, Jr. . |
| 4,450,960 | 5/1984 | Johnson . |
| 4,458,017 | 7/1984 | Horwath et al. ........................... 435/94 |
| 4,496,397 | 1/1985 | Waite . |
| 4,501,814 | 2/1985 | Schoenrock et al. . |
| 4,548,605 | 10/1985 | Iwamoto et al. . |
| 4,622,425 | 11/1986 | Gagne . |
| 4,664,256 | 5/1987 | Halskov . |
| 4,812,320 | 3/1989 | Ruzek . |
| 4,830,858 | 3/1989 | Payne et al. . |
| 4,892,579 | 1/1990 | Hazelton . |
| 4,895,726 | 1/1990 | Curtet et al. . |
| 4,895,729 | 1/1990 | Powrie et al. . |
| 4,919,955 | 4/1990 | Mitchell . |
| 4,946,326 | 8/1990 | Schvester et al. . |
| 4,965,165 | 10/1990 | Saccocio et al. . |
| 4,971,813 | 11/1990 | Strobel et al. . |
| 5,004,623 | 4/1991 | Giddey et al. . |
| 5,006,222 | 4/1991 | Sequeria, Jr. . |
| 5,021,251 | 6/1991 | McKenna et al. . |
| 5,030,778 | 7/1991 | Ransford . |
| 5,045,529 | 9/1991 | Chiang . |
| 5,064,070 | 11/1991 | Higashiyama . |
| 5,108,656 | 4/1992 | Schvester et al. . |
| 5,128,160 | 7/1992 | Fath et al. . |

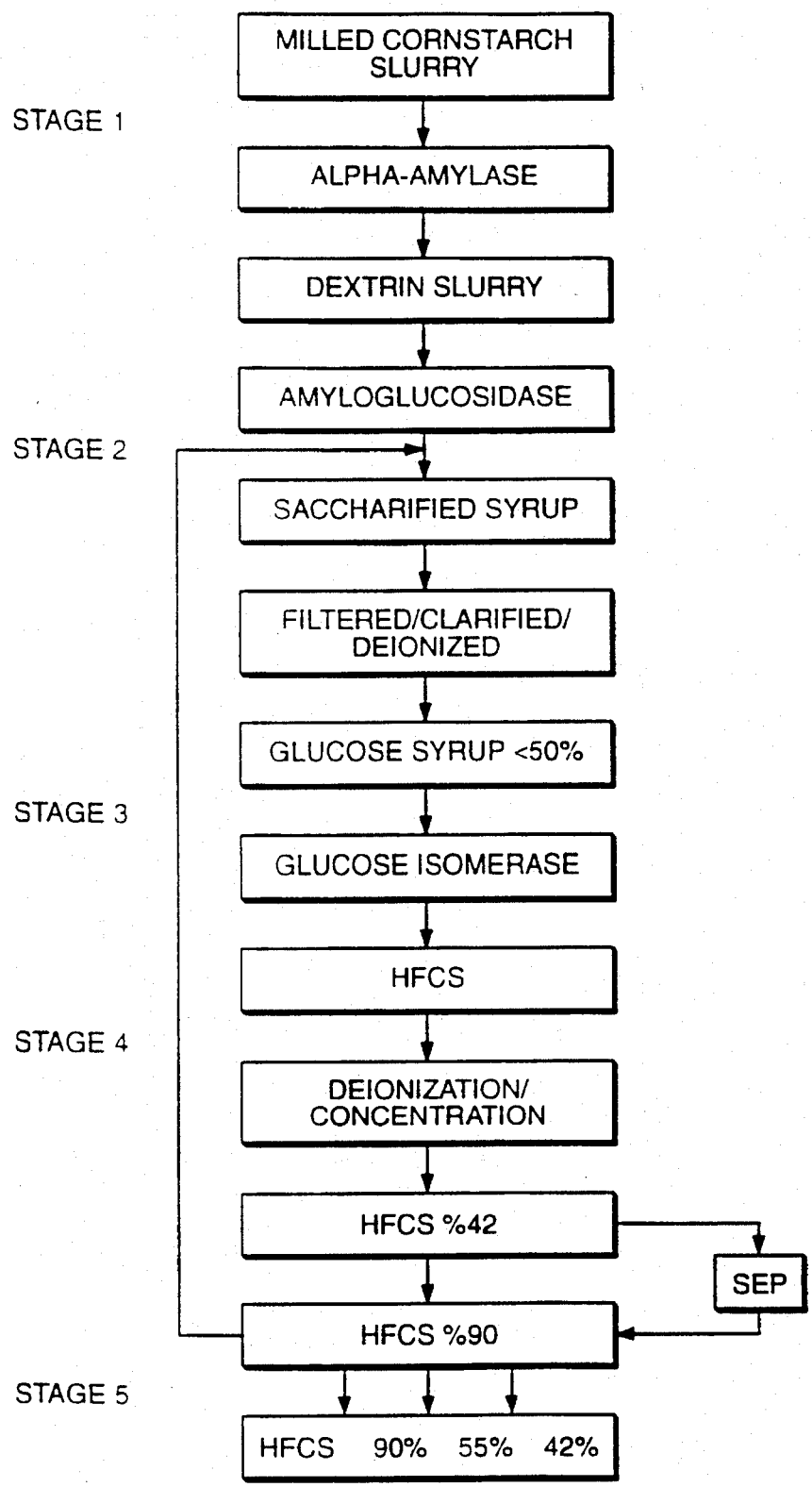
FIG._1

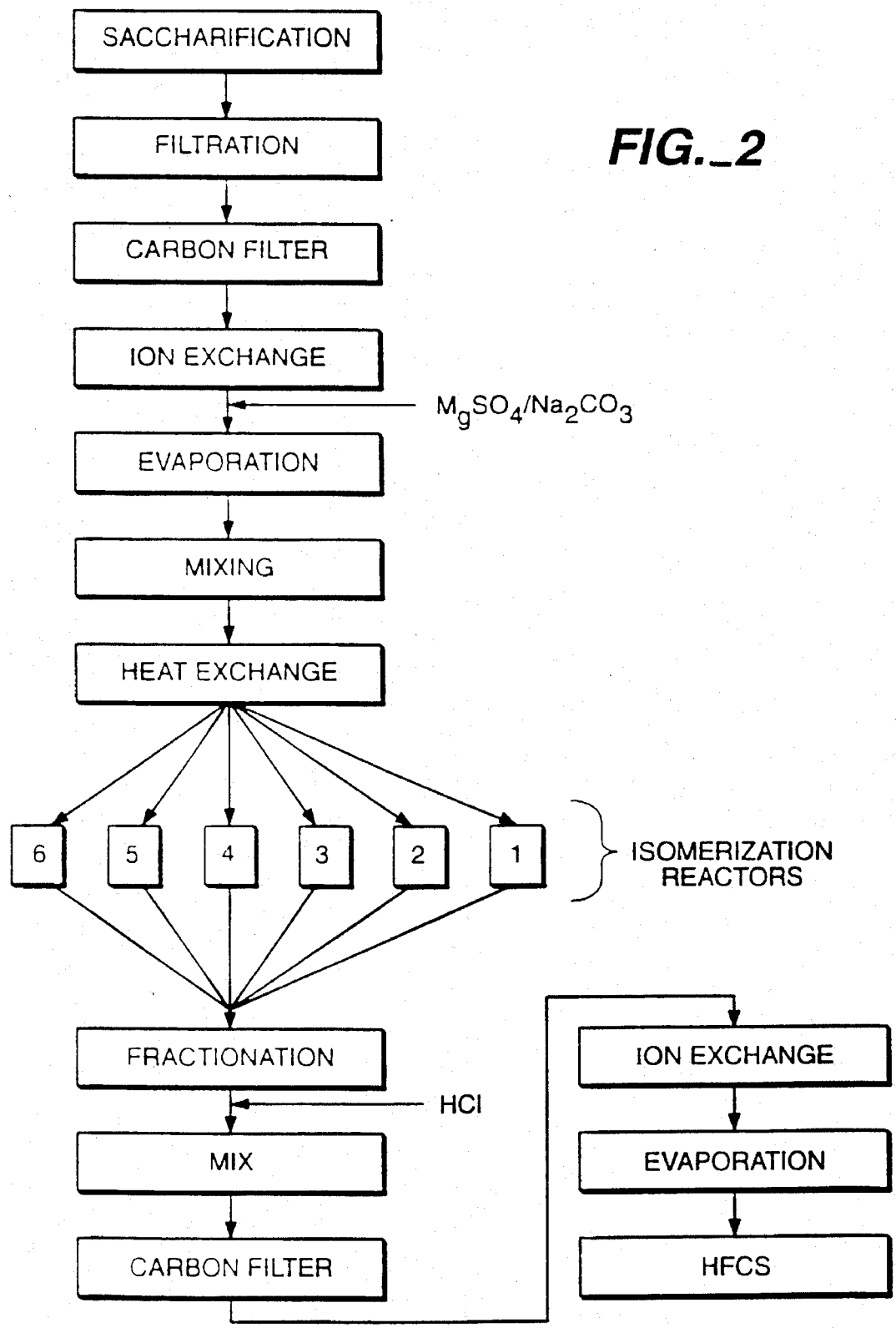
FIG._2

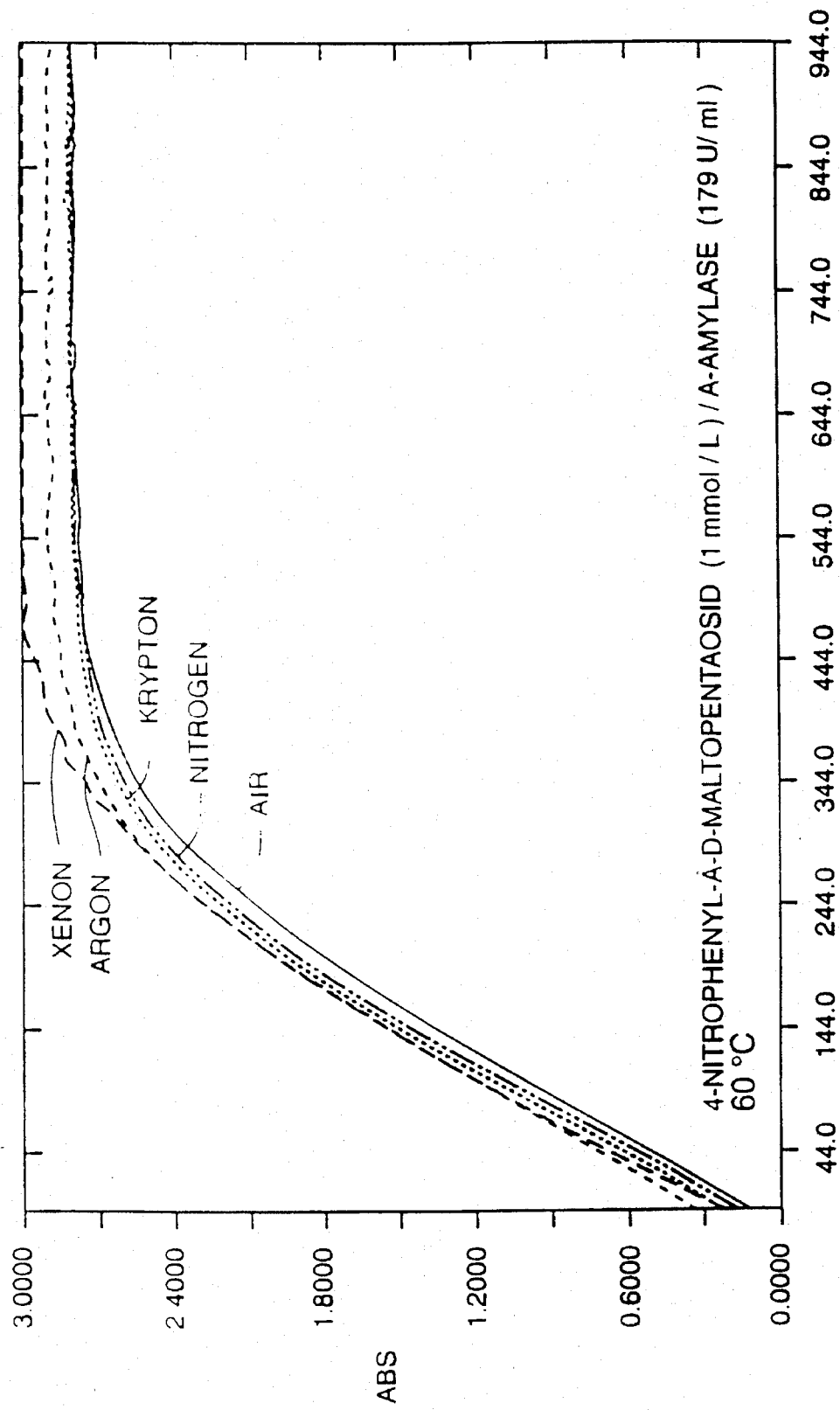
FIG._3

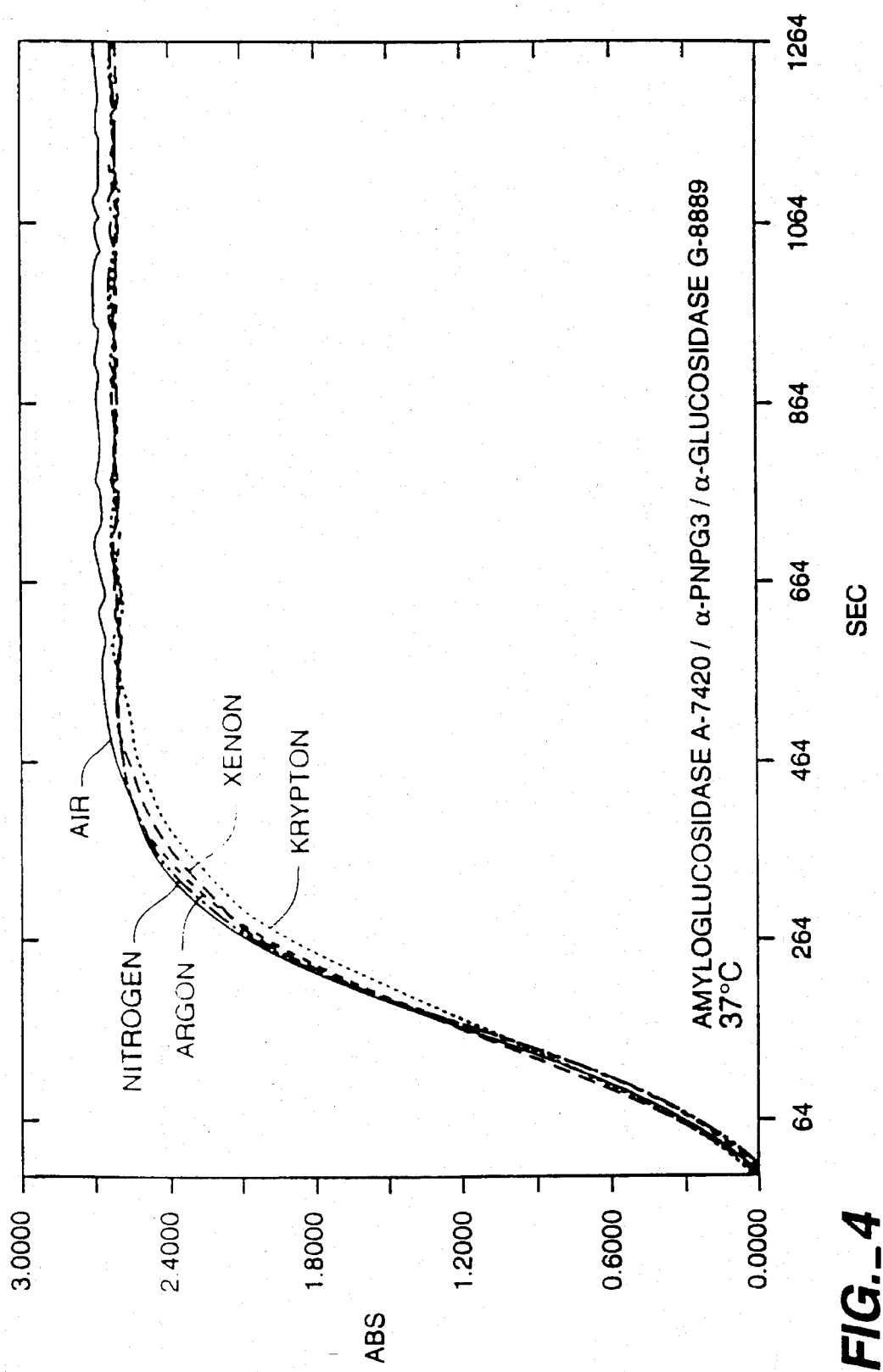
FIG._4

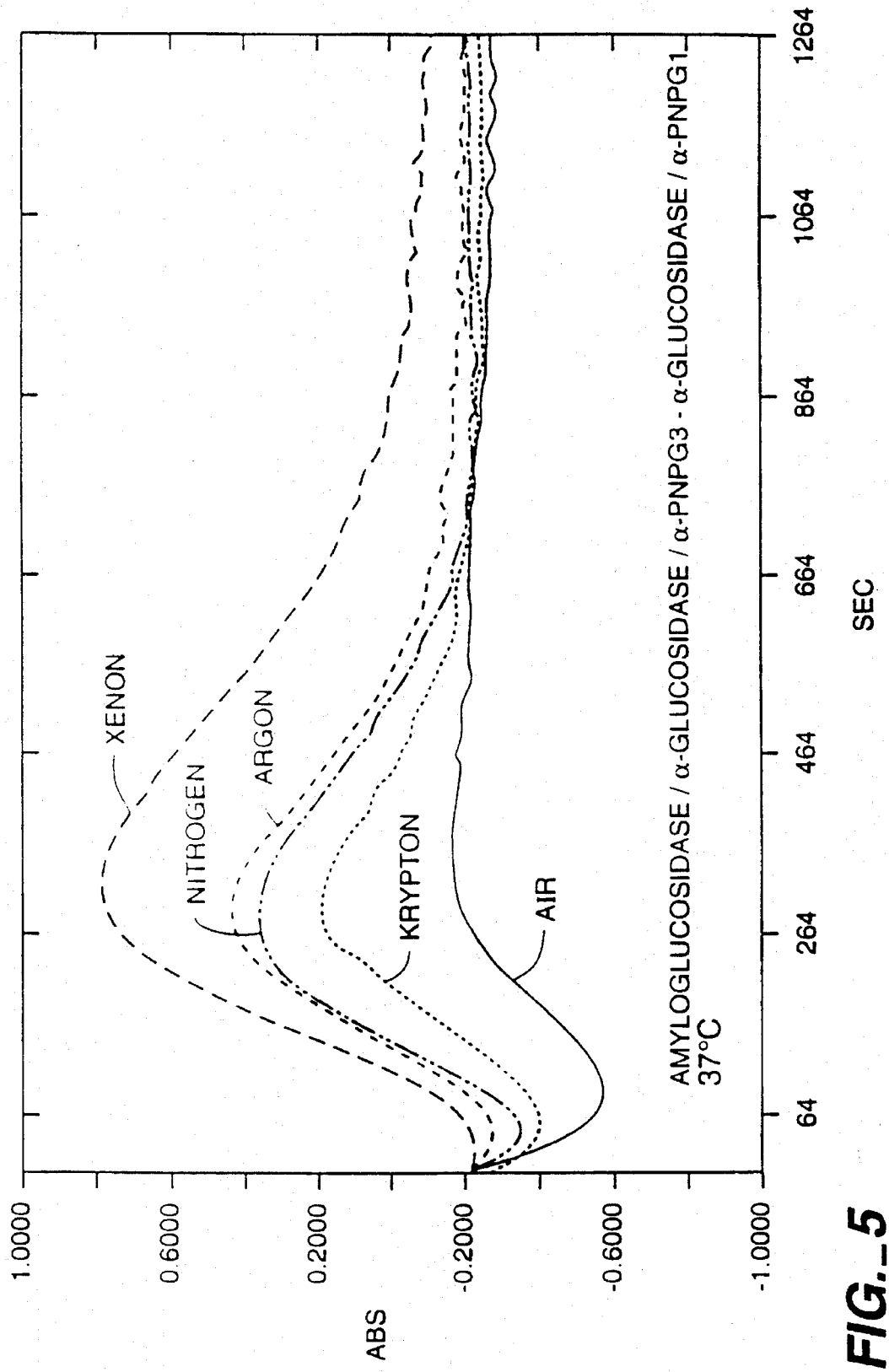
FIG._5

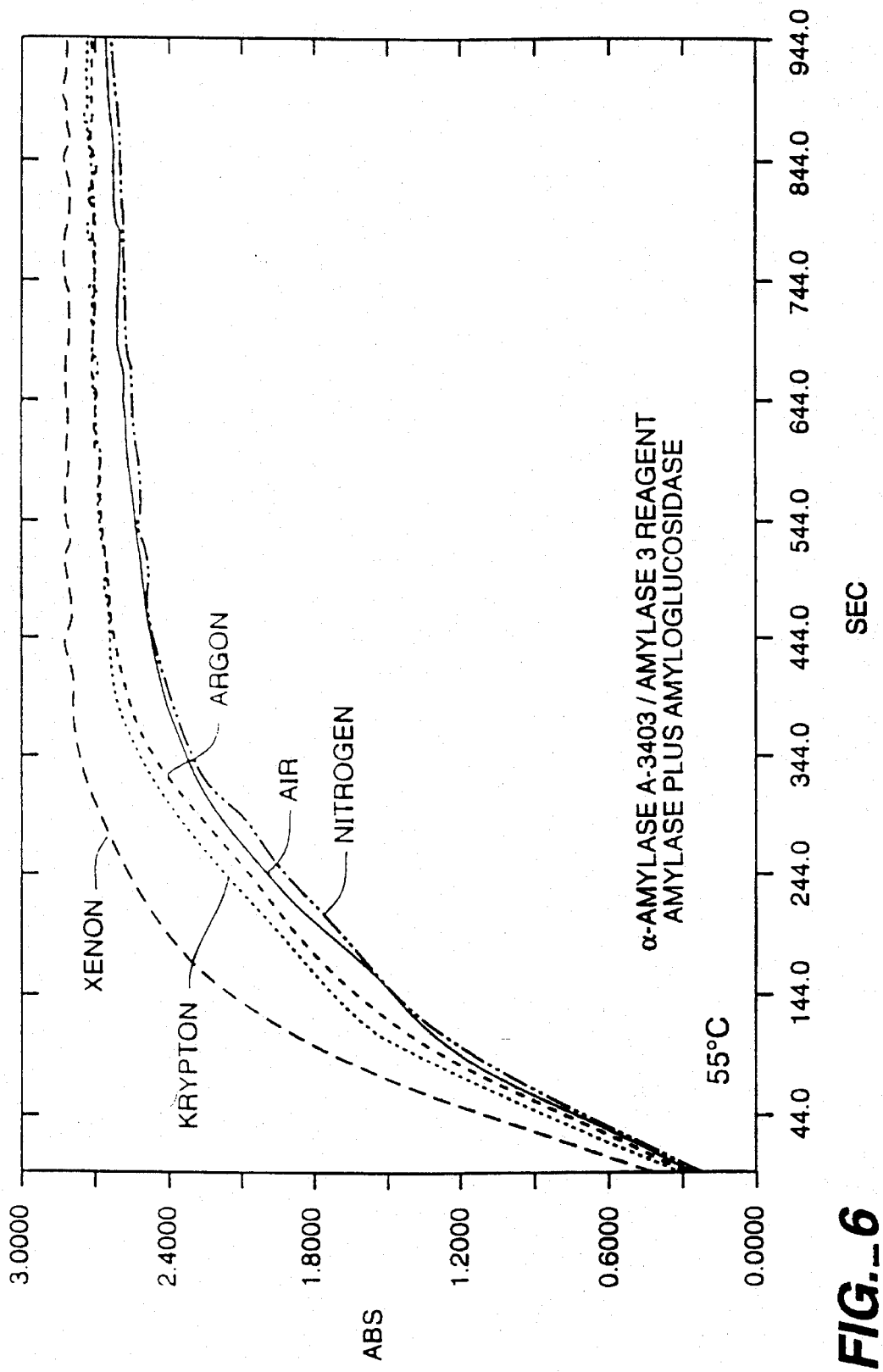
FIG._6

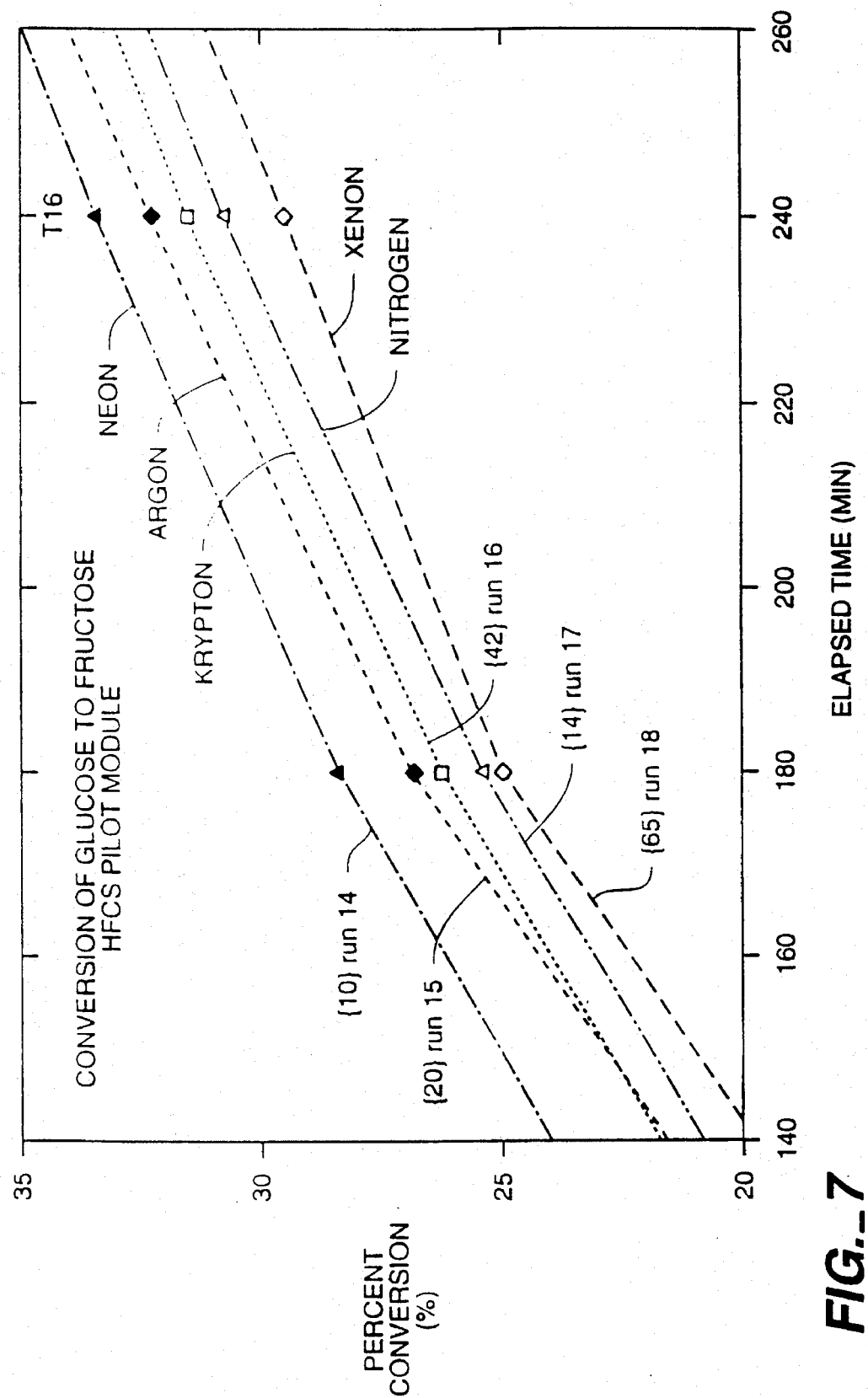
FIG._7

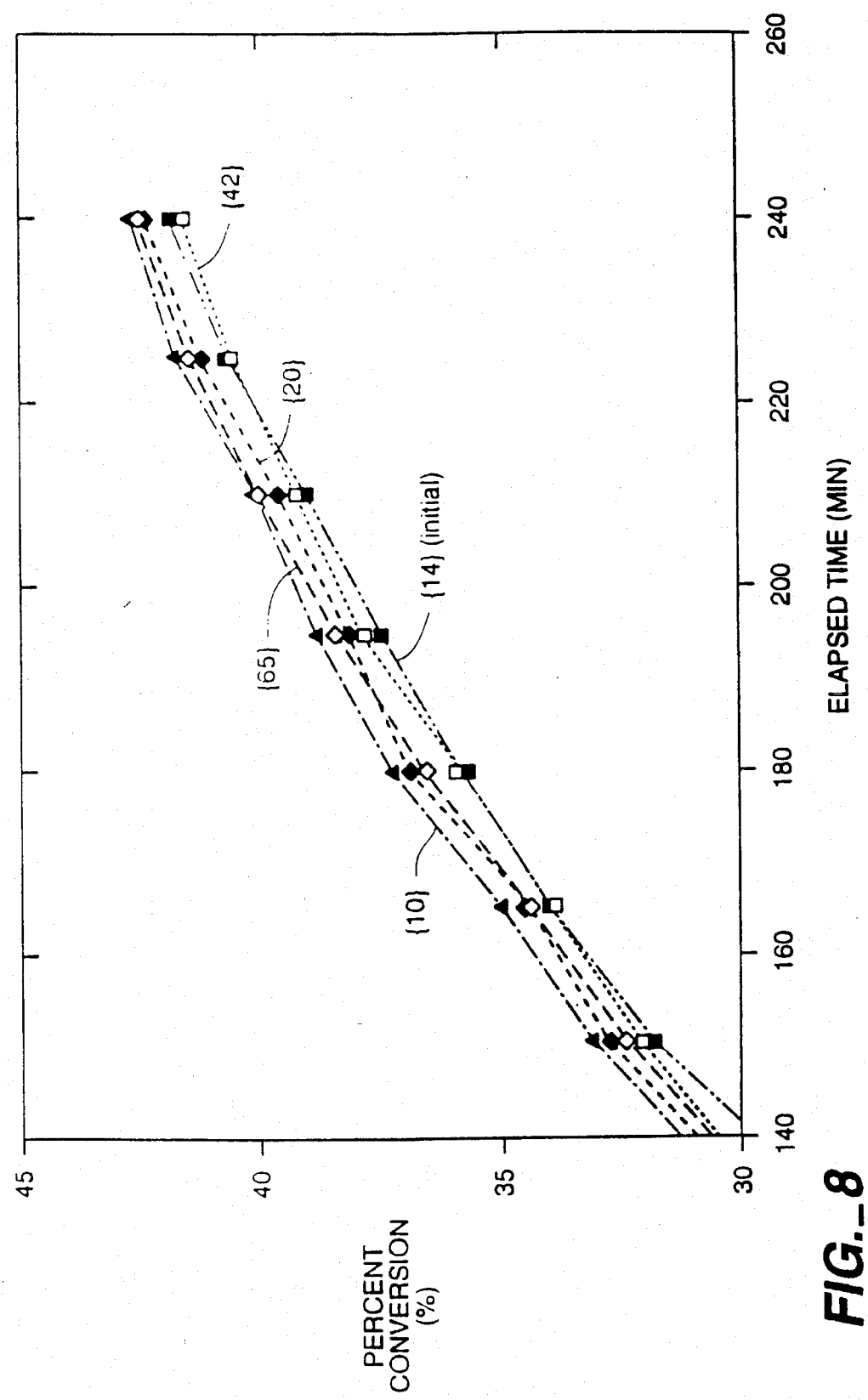
FIG._8

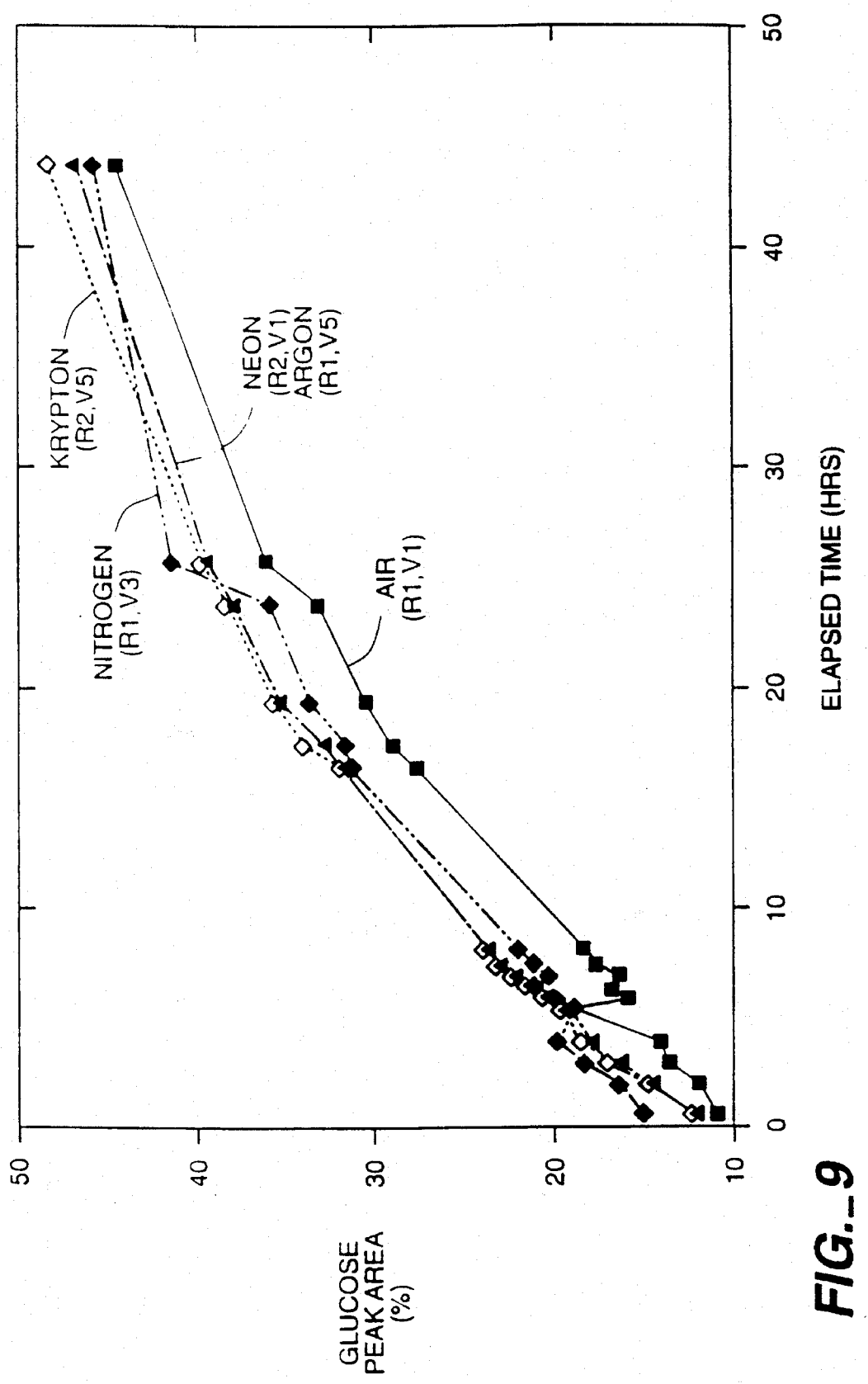
FIG._9

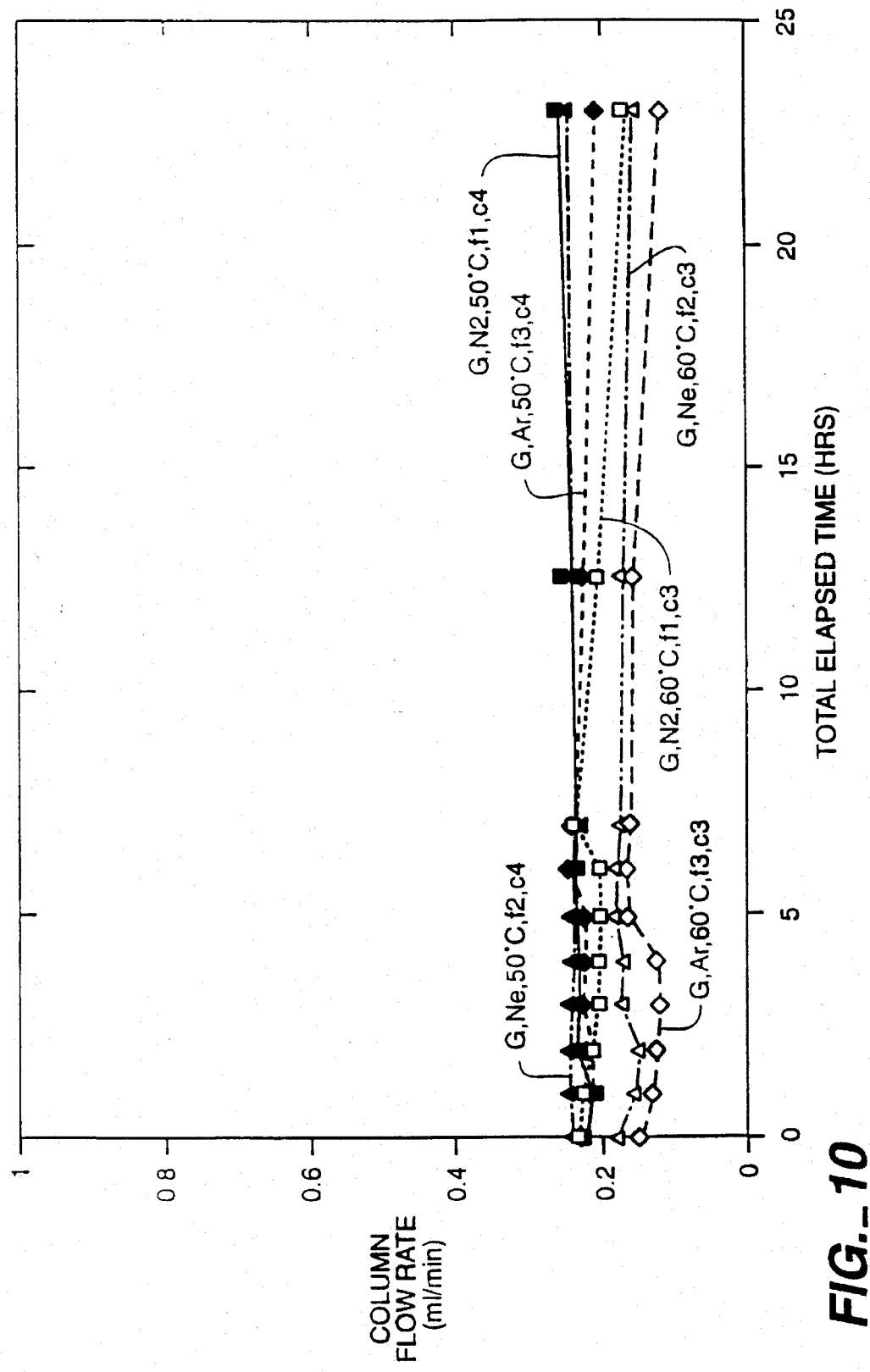
FIG._10

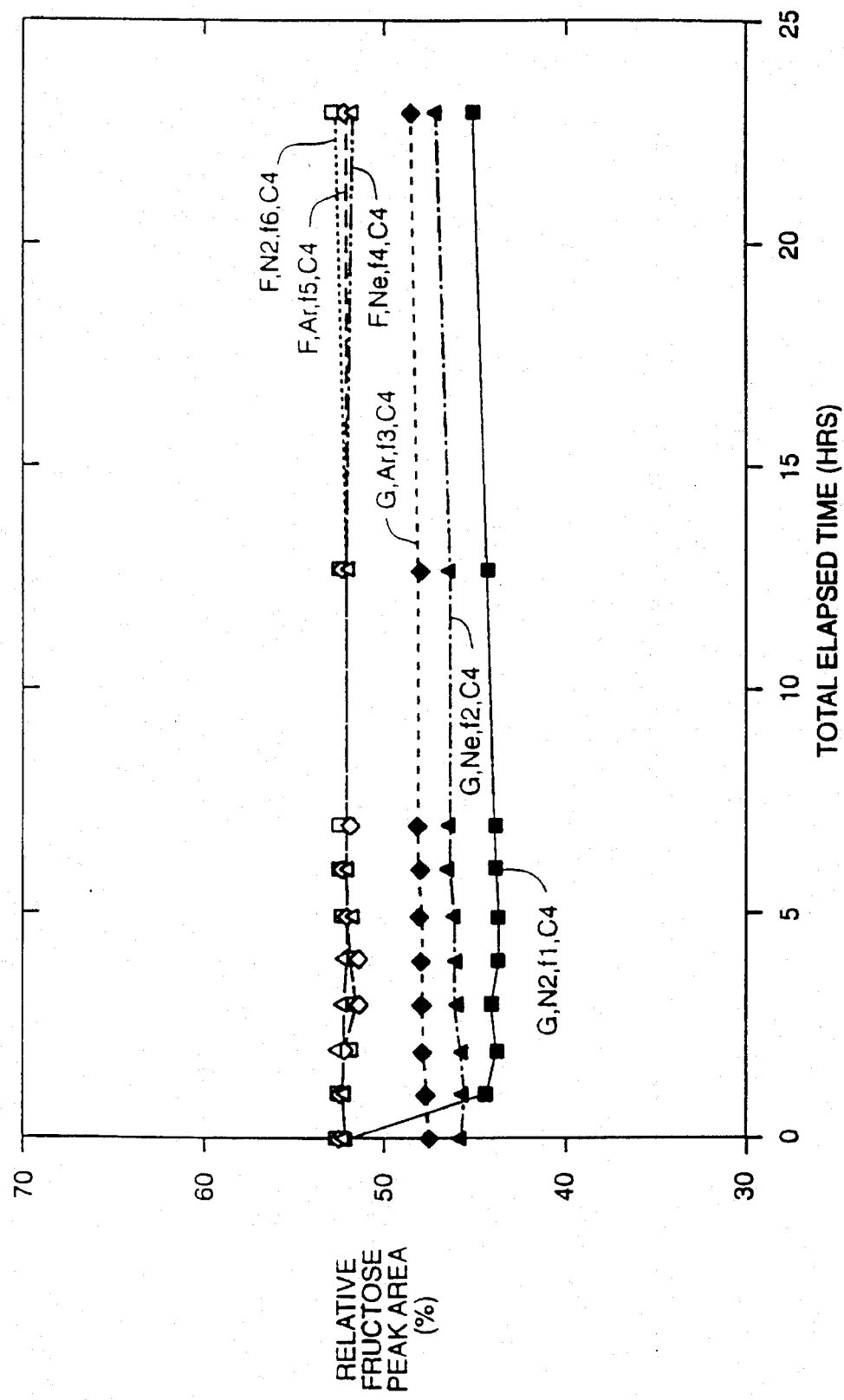
FIG._11

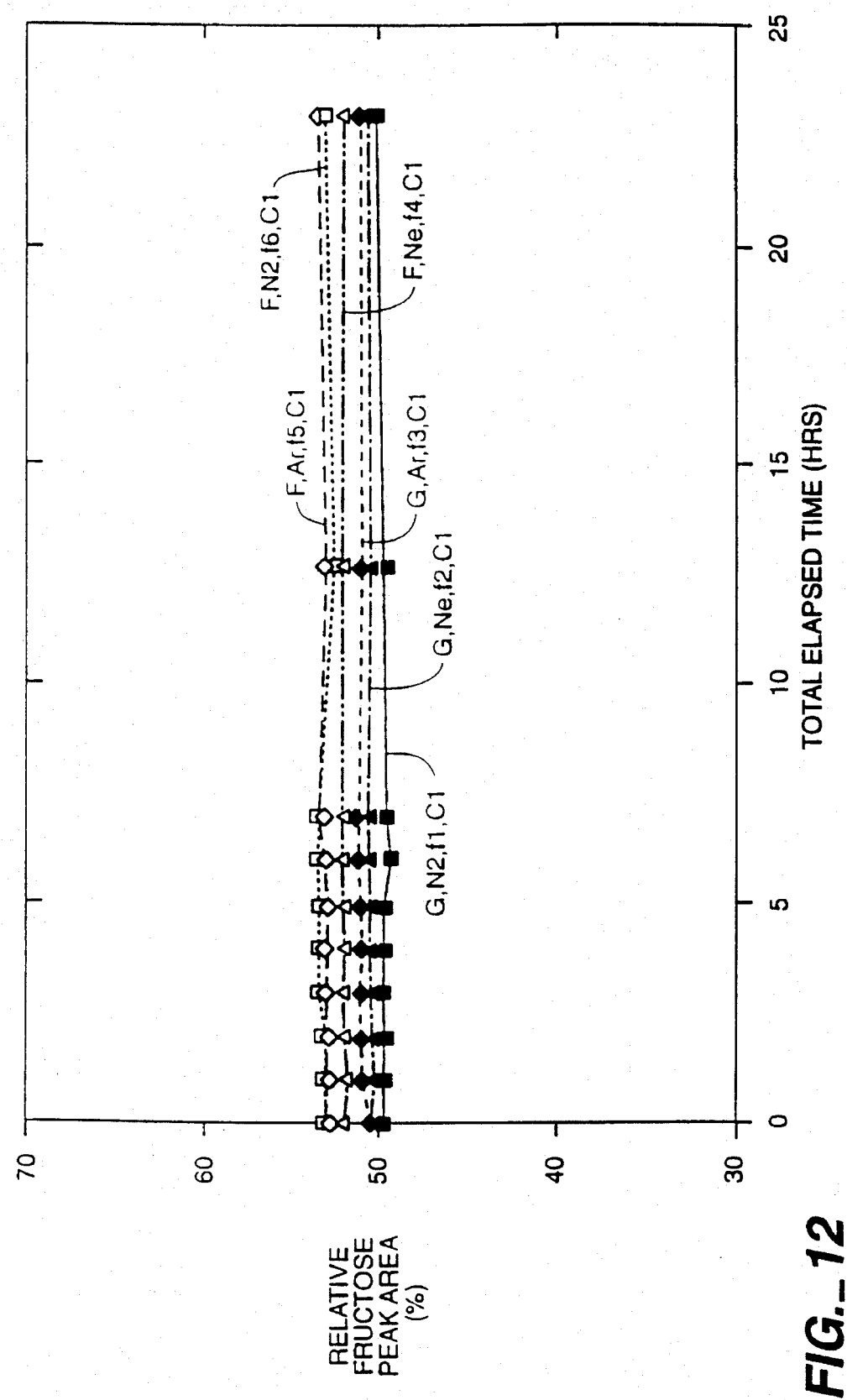
FIG._12

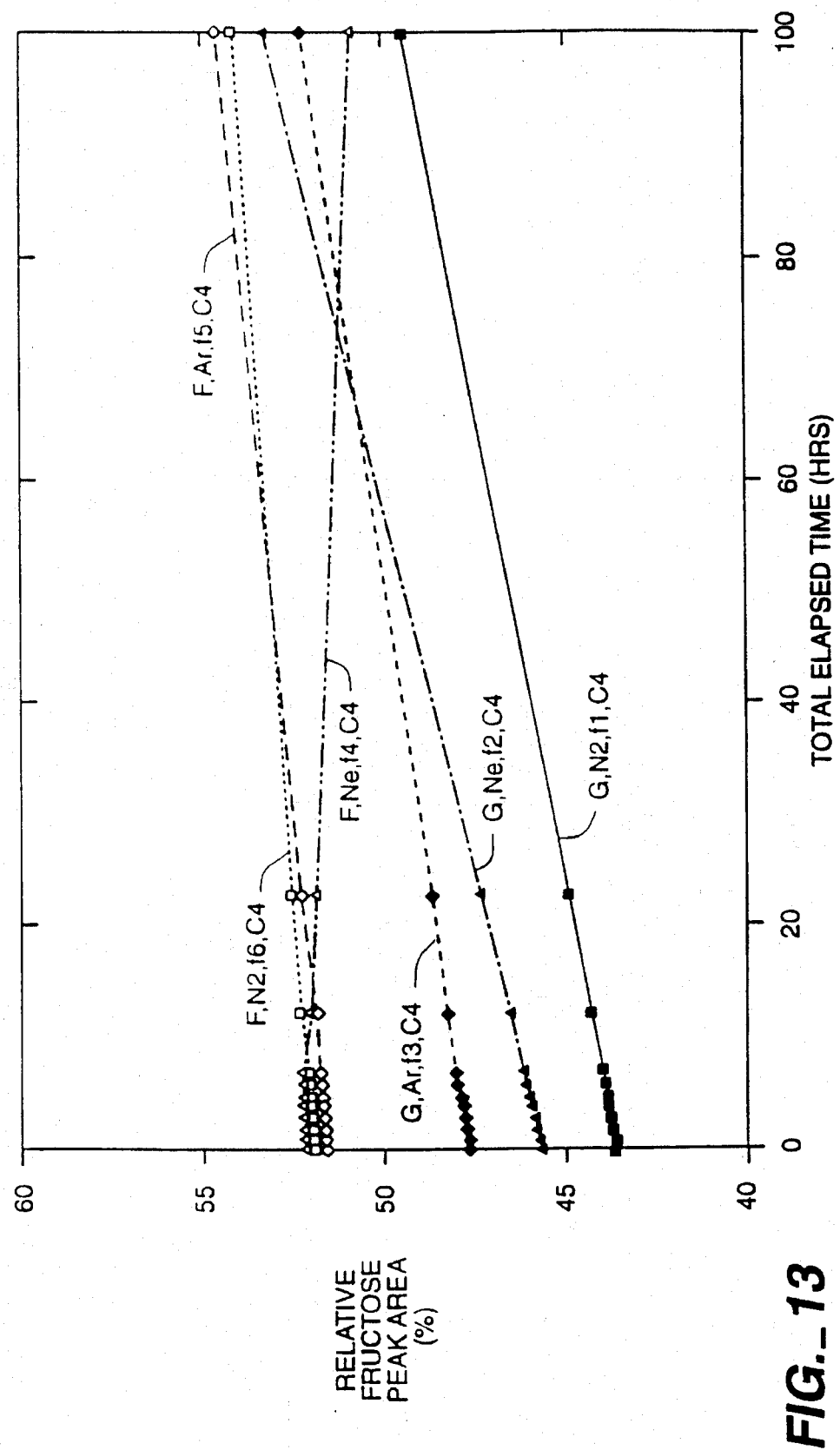
FIG._13

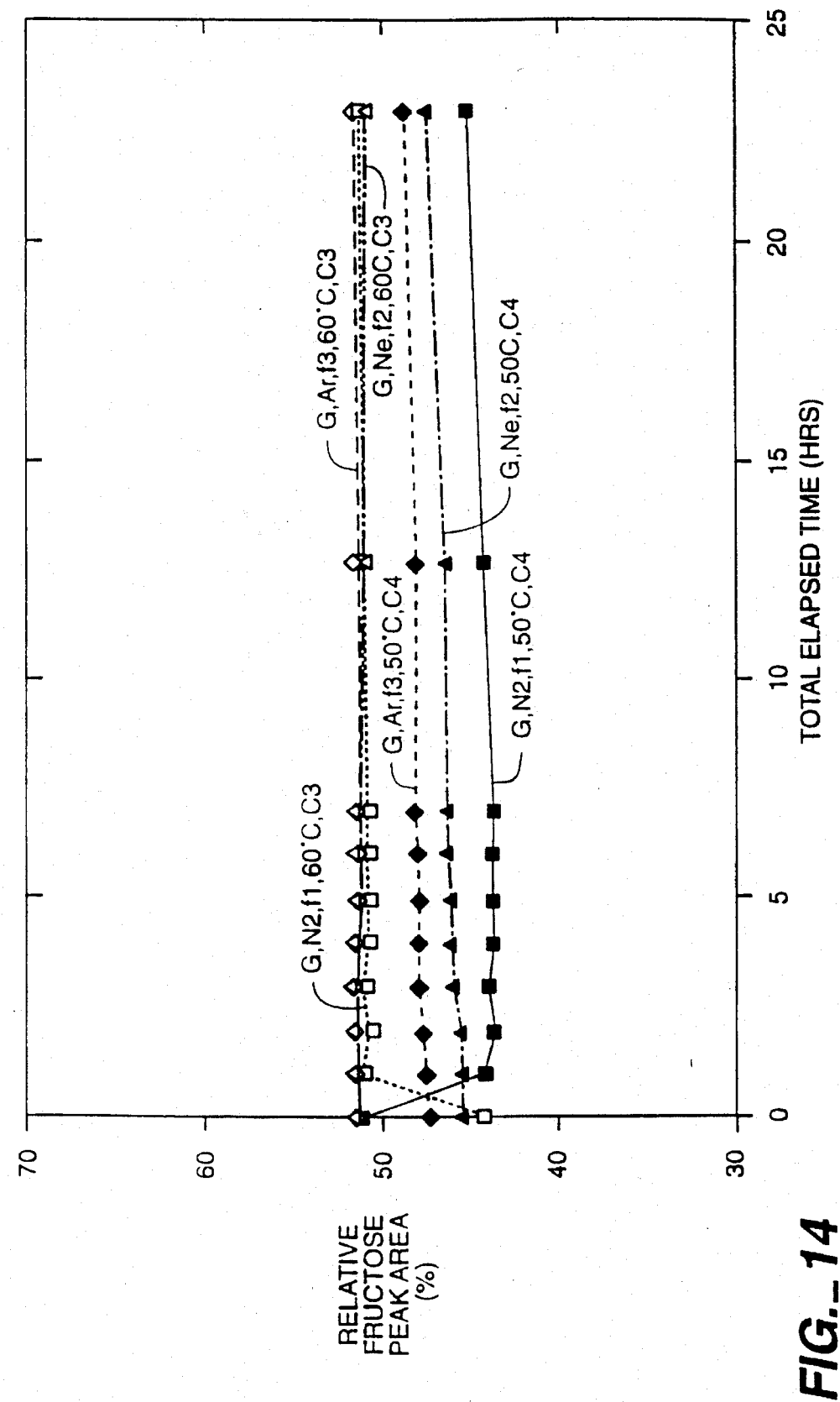
FIG._14

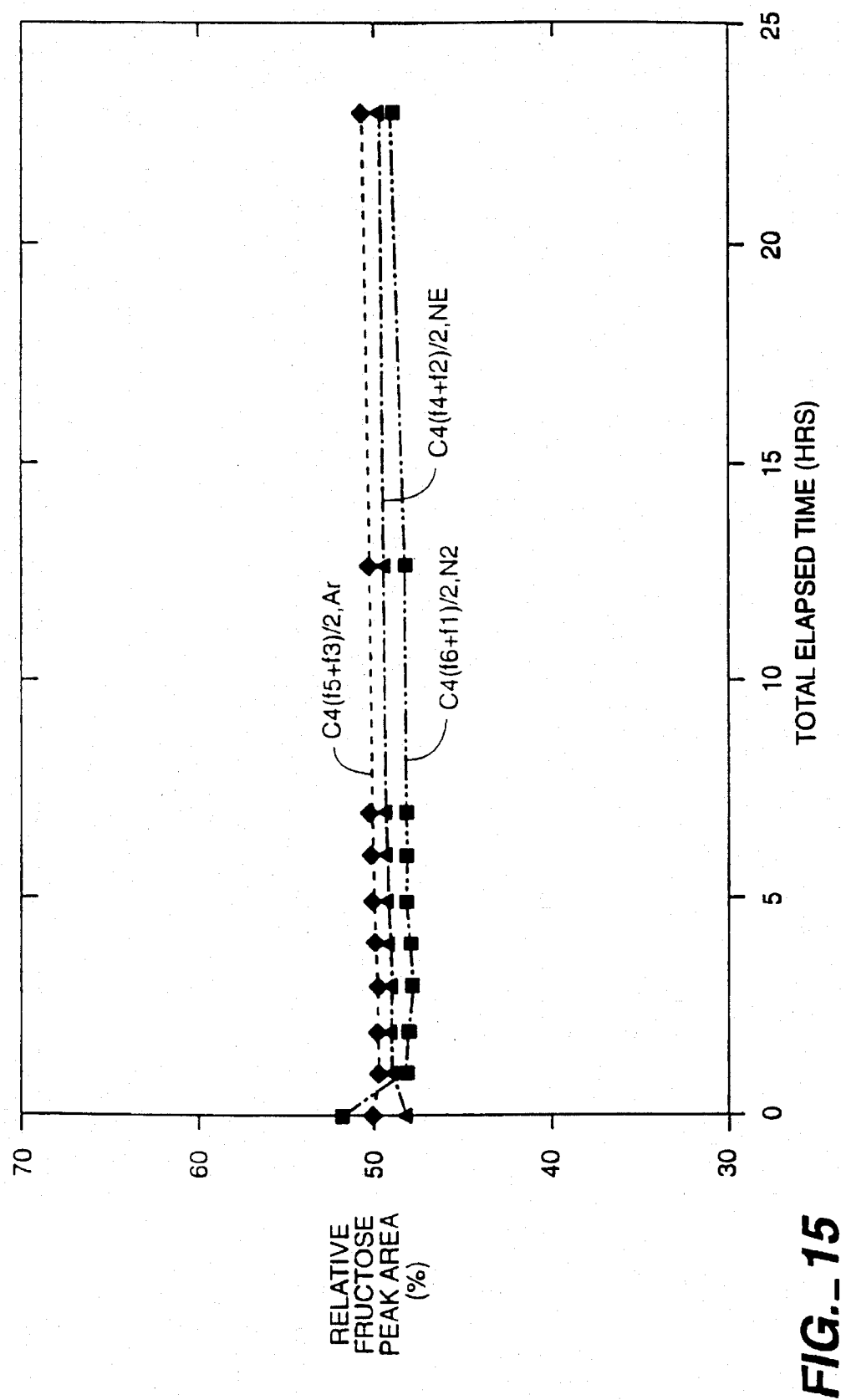
FIG._15

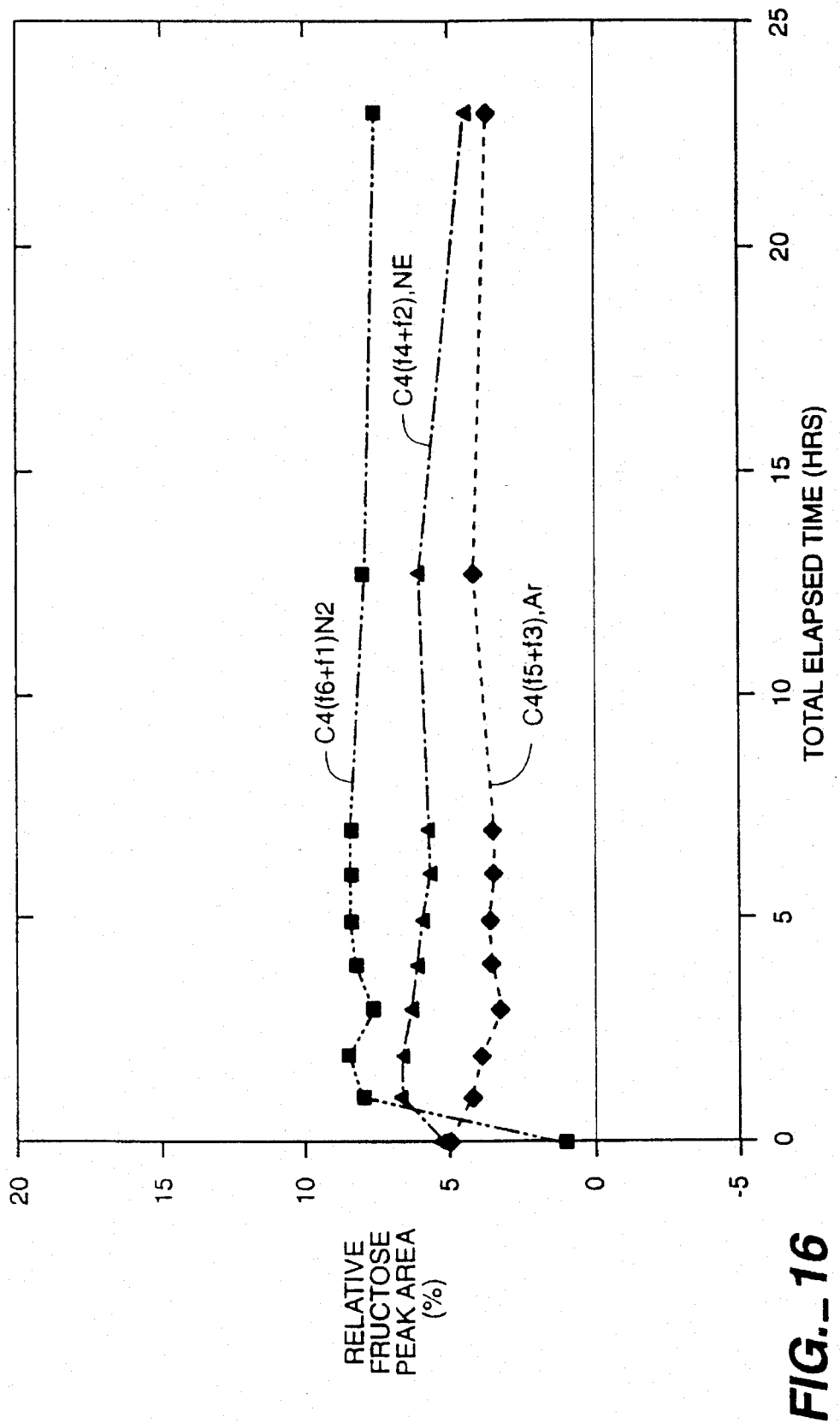
FIG._16

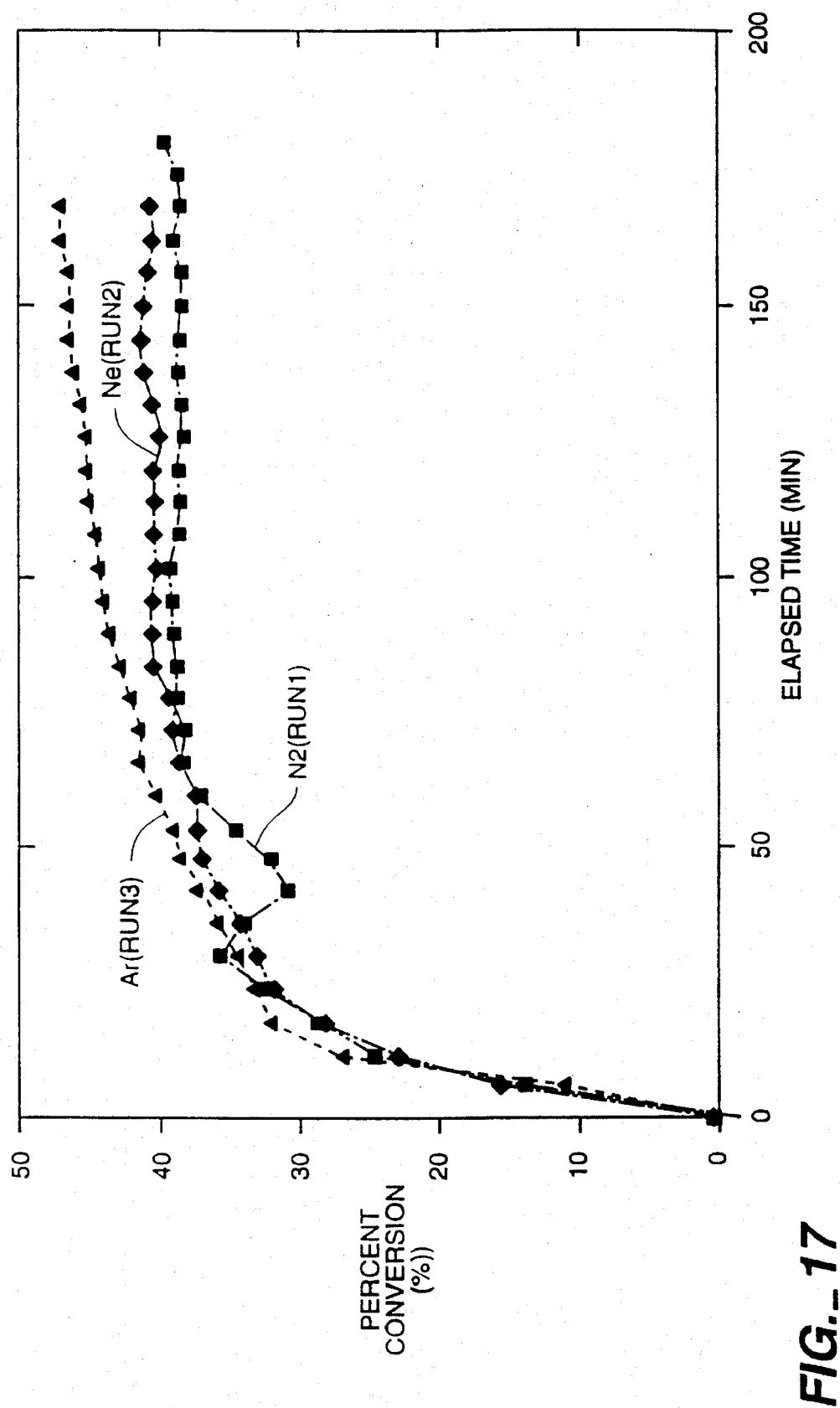
FIG._17

METHOD OF PRODUCING HIGH FRUCTOSE CORN SYRUP FROM GLUCOSE USING NOBLE GASES

This application is a Continuation of application Ser. No. 07/816,732, filed on Jan. 3, 1992, now abandoned.

BACKGROUND OF THE INVENTION

1. Field of the Invention

The present invention relates to a process for producing high fructose corn syrup from glucose using noble gases.

2. Description of the Background

Wild honey is the oldest sweetener known to man, however the use of cane sugar as a sweetener dates back at least 8,000 years to the South Pacific. The sweetness of cane sugar approximates that of honey.

It was determined in 1744 that the sugar isolated from sugar beets is identical to the sugar derived from sugar cane. Thereafter, sucrose, manufactured from cane or sugar beets, being much more abundant than honey, became the sweetener of commerce. This position remained unchallenged until the development of high fructose corn syrup, a corn sweetener.

The development of corn sweeteners dates to 1811, when it was discovered that starch yielded a sweet substance when heated with acid. It was not until 1940, however, that the discovery, isolation and application of various carbohydrase enzymes afforded many new corn syrups having a variety of syrup properties. See L. E. Coker and K. Venkatasubramanian (1985). Starch Conversion Processes. Ch. 29, M. Moo-Young (ed.) Comprehensive Biotechnology, Vol. 3, H. W. Blanch, S. Drew and D. I. C. Wang (eds.), Pergamon Press, New York, N.Y., pp. 777–787.

More recently, glucose isomerase, which converts glucose to its sweeter isomer, fructose, was commercially developed. In the wake of this development, the enzymatic transformation of glucose to fructose was first introduced to corn sweetener production in 1967. The first high fructose corn syrup, commonly referred to as HFCS, contained 15% fructose. The manufacturing process, known as isomerization, originally involved the direct addition of isomerase enzymes to a dextrose substrate and a batch reactor. Further process improvements afforded HFCS products containing 42 and 55% fructose. Many producers of HFCS now further concentrate the fructose, using a chromatographic technique, and supply the concentrated material as a sweetener. See Verhoff, F. H. et al (1985). Glucose Isomerase. Ch. 42, M. Moo-Young (ed.), Comprehensive Biotechnology, Vol. 3, H. W. Blanch, S. Drew and D. I. C. Wang (eds.), Pergamon Press, New York, N.Y., pp. 837–859.

HFCS is now the most widely used sweetener in beverages and is used as well in the bakery, dairy, and canned foods industries. As noted above, HFCS is produced from corn, and it the most popular of the corn sweeteners. Other corn syrups contain glucose and dextrose; however fructose is the sweetest isomer. Through a process called wet-milling, the starch from corn is converted into corn syrup, and this syrup is then filtered to extract a syrup of highly concentrated fructose. There are presently three types of HFCS commonly sold in the United States: HFCS-42, -55, and -90, representing the percentage of fructose in the mixture. HFCS-55 is manufactured by blending 42 and 90% fructose, and is the highest value and most used of the three.

HFCS is attractive as a substitute for sugar because it is generally lower-priced and sweeter, thus necessitating smaller input per unit of output. Although HFCS is a liquid of comparable sweetness to sugar, it has different physical properties. Thus, HFCS cannot substitute for sugar in all products. For instance, baked products require sugar to ensure proper browning and for texture; jams and jellies require sugar to gel properly.

The soft drink industry accounts for approximately 75% of the demand for HFCS in the U.S. each year. Of the HFCS types available, HFCS-55 accounts for the bulk of the HFCS use in the beverage industry, representing 95% of all caloric sweeteners used in beverages. The other major type, HFCS-42, is more commonly used in the baked goods and dairy industry as a substitute for sugar in products in which color and texture, or gelling properties, are not affected by HFCS. Because of its high concentration of fructose, HFCS-90 is used primarily in reduced calorie foods such as jams and jellies.

A crystalline form of fructose can be produced from HFCS, but until recently the commercial price of this form was not competitive with the other versions. However, a cheaper production process was introduced in 1987, and experimental production of this form is continuing. Most of the crystalline form is currently used as part of a sweetener blend. Crystalline fructose may become a substitute for sugar in some new products, but the market appears to be limited.

Because of its low cost, corn has become the primary raw material source of starch syrups and sugars, including HFCS. Corn is processed into starch through a method called wet milling. In addition to the production of starch, the initial raw material in the HFCS production process, the wet milling process produces several valuable by-products that can be sold by the miller for a profit as well. Thus, these by-products serve to enhance the attractiveness of HFCS production by lowering the final cost to the producer of HFCS. In addition to starch, the wet-mill process also produces 13 pounds of gluten feed (per bushel of corn used), 2.75 pounds of gluten meal, and 1.6 pounds of oil. In terms of percentage of output produced, starch (the HFCS precursor) is the primary product, representing 67.2% of the output from a bushel of corn. Feed accounts for 19.6% of output; germ (corn oil precursor), 7.5%; and meal, 5.7%.

Corn starch is the initial raw material in the HFCS production process. Through a series of four major processing stages, the starch is converted to 42% HFCS. The major stages are: (1) conversion of starch to dextrose feedstock; (2) preparation of high quality dextrose feedstock for isomerization; (3) isomerization of the feedstock to fructose, the major and most significant stage in the process; and (4) secondary refining of the fructose product. If required, a fifth stage can be added in which additional refining of the 42% solution can be used to produce 55% and 90% fructose syrups. A diagram of the conventional 5-stage process is given in FIG. 1. Each Stage from that figure is discussed below.

Stage 1: First Enzymatic Step: alpha-amylase. The first stage converts the starch slurry to dextrose. The starch slurry is initially a mixture of amylose (approx 15-30%) and amylopectin (approx 70–85%). Several steps are involved in the production of dextrose from starch. First, the starch slurry is subjected to a high temperature treatment in which the starch granules burst and the starch becomes gelatinized. This gelatinized starch is then thinned by both high temperature and hydrolysis by alpha-amylase. This step produces liquid, less viscous and lower molecular weight dextrin products. This step takes approximately 130 minutes.

Second Enzymatic Step: amyloglucosidase. Following this liquefication and dextrinization, the dextrin products are in turn subjected to stepwise hydrolysis by amyloglucosidase to form a glucose syrup. This is referred to as saccharification, a continuous process which can take as long as 75 hours, depending on the amount of enzyme present. The end result of the saccharification process is a high dextrose (94–96% dextrose) hydrolyzate that is further refined in Stage 2.

Stage 2: The dextrose from Stage 1 is refined to produce a high quality feedstock necessary for the isomerization process in Stage 3. The refining process reduces the impurities such as ash, metal ions, and proteins which can impair the efficiency of the isomerization enzyme in Stage 3. In the refining process, the dextrose is subjected to a series of filtration steps to remove protein and oil. Next, the color of the liquor is removed through a series of granulated carbon columns. Then, the liquor is subjected to an ion-exchange system in which it is deionized. Lastly, the liquor is evaporated to the proper level for the next stage and treated with magnesium ions to inhibit any calcium ions that may interfere with the isomerase activity in Stage 3.

Stage 3: Third Enzymatic Step: Glucose Isomerase. This stage, in which the dextrose liquor is isomerized to high fructose corn syrup, is the heart of the HFCS process.

The isomerization stage converts the glucose to a much sweeter, and thus more valuable, fructose product. The key development that makes this enhanced value possible is the commercial development of immobilized glucose isomerase, a bound enzyme which can withstand the elevated temperatures of the process. The cost of the isomerization enzymes is a significant part of the total operating cost of the HFCS process. Thus, much research effort has been devoted to the economics of the activity of the enzyme and especially the rate of its decay.

Use of immobilized enzyme reactor systems (vs batch reactions, with their much longer reaction times) is the common form in the industry. The critical variable in this stage is the activity of the enzyme, which controls the rate of conversion of dextrose to fructose and determines the quality and fructose content of the product. This is a functional property of the enzyme itself and is modified by reaction conditions. The activity of the enzyme decays through time in a relatively regular manner, and the reactor system is designed and operated to minimize the fluctuations in activity resulting from this decay. For instance, the flow of the dextrin is continuously adjusted so that the residence time of the dextrin can increase to match the reduction in enzyme activity to achieve a constant conversion level through time. In addition, parallel reactors are used to increase operational flexibility. In general, at least eight isocolumns are operated in parallel and independently of the others so that each column can be put on- or taken off-line as needed.

The activity of the enzyme system is usually characterized by what is referred to as a half life. The half life of the enzyme is the amount of time that is required for the enzyme activity to be reduced by half. The enzyme system is usually operated for at least two half-lives and then replaced. Variables affecting half-life of the enzyme, and thus replacement costs, include the allowable variance in flow, pH, salt concentrations, temperature, dry solids content, metal ion concentrations, required production capacity of the processor, the number of isocolumns in parallel, and the average decay rate of the individual columns. Indeed, the economics of the HFCS process is generally analyzed in terms of costs per pound of enzyme utilized. The physical properties of the enzyme system determine its productivity and its half-life; these two parameters in turn affect the size of the reactor necessary to produce the desired conversion level and throughput of HFCS.

In general, HFCS producers seek to reach an optimal operation condition across several parameters including enzyme longevity and activity, flow rate and temperature.

The glucose isomerase system is the largest volume use of an immobilized enzyme in the Unites States. There are a number of commercial suppliers of the isomerization system.

Many of the suppliers sell fixed whole cells with isomerase activity, although other suppliers sell different immobilized forms, or a pure, isolated enzyme system. The enzyme system is used within the plant in a packed-bed reactor consisting of parallel columns of enzyme material. Most catalysts/enzyme systems are in particulate form (dry pellets). The systems available commercially vary as to the organism from which the isomerase is derived, the immobilization carrier, and the binding procedures used by the producer.

The most important variables affecting the design of a reactor system, and thus the productivity of the isomerization process include the enzyme loading factor, catalyst packing density, operational stability of the catalyst, or reactor half-life, transport efficiencies, enzyme contact and residence time.

The enzyme loading factor refers to the amount of enzyme (and thus catalytic activity) present in the immobilization system. This factor is influenced primarily by the immobilization process used to produce the enzyme system, and is determined by the enzyme producer. Load factor varies according to the relative amount of cells present, if the system is a fixed cell system, and the extent of enzyme inactivation, or loss of activity through the various enzyme preparation stages.

Catalyst packing density refers to the amount of enzyme complex present per unit volume of reactor. This is influenced in part by such variables as pressure and reactor configuration, whether linear bed or spiral.

Reactor half-life, the amount of time required to reduce the enzyme activity by half, depends on such factors as the bacteria or the organism used to produce the enzyme, and is also primarily a function of the particular enzyme system purchased.

Transport efficiency involves the rate of flow of substrate through the membrane system. Since it can be slower than the reaction time itself, the transport time of the substrate can greatly affect overall productivity.

Finally, enzyme contact and residence time, which contribute to the efficiency with which the enzyme operates on the substrate, is a function of reactor design (e.g., column size and flow rates).

Stage 3 can take as long as 4 hours.

Because of the biochemical kinetics of the conversion process, the primary product of Stage 3 is a 42% HFCS solution, which contains as well 52% unconverted dextrose, and 6% oligosaccharides. Further processing of the HFCS solution involves secondary refining of the 42% portion in Stage 4.

Stage 4: Color and ash are removed from the 42% HFCS through carbon filtration and ion-exchange systems. Stage 4 can also involve evaporation of the 42% solution to solids for shipment.

As discussed above, 42% HFCS is used primarily in bakery goods and dairy products. An additional stage (Stage 5) is required to convert 42% HFCS to 90% HFCS, which is in turn mixed with 42% to produce a third type of HFCS, 55%. 55% HFCS is used in the soft drink industry, and is the higher value HFCS product.

Stage 5: This stage involves the selective concentration of the 42% fructose: 52% dextrose product of Stage 4 to a higher concentration fructose product (90%) and its blending with the original 42% to produce other concentrations.

Since fructose preferentially forms a complex with cations, while dextrose does not, various purification processes utilize this difference either through chromatographic fractionation using organic resins or through inorganize resins in packed bed systems. The immediate product of Stage 5 is a Very Enriched Fructose Corn Syrup (VEFCS) with a 90% fructose concentration. This VEFCS can be used in turn with the 42% HFCS to produce a product with concentrations between 42% and 90% fructose, the most common being, as stated above, 55%.

The processes required to produce HFCS from corn starch is portrayed schematically in FIG. 2. FIG. 2 restates the 5-stage process given in FIG. 1 in terms of processing stages within the HFCS-producing plant.

Saccharification corresponds to Stage 1 of the process detailed above in Section 2, in which the initial input of corn starch is converted to a dextrose feedstock. Purification and pretreatment, in which the dextrose feedstock is refined further before the isomerization to HFCS, correspond to Stage 2. The isomerization process, in multiple reactors, corresponds to Stage 3. Finally, the post-treatment processes, in which impurities are removed (Stage 4) and the HFCS can undergo further refinement to higher HFCS concentrations, correspond to Stages 4 and 5.

Thus, the production of high-fructose corn syrup is generally accomplished by the large-scale enzymatic conversion of corn starch to fructose. The process steps entail a saccharification step which consists of enzymatic hydrolysis of corn starch to dextrins and then to glucose by the action of amylase and amyloglucosidase followed by an isomerization step which entails passing saccharified syrup over a column of immobilized glucose isomerase resulting in the conversion of glucose to fructose.

The isomerization step is one of the primary process-regulating steps, and represents a major expense in the process. See Novo Industri A/S (1985.) Novo Enzyme Information. IB No. 175d-GB. Continuous Production of Fructose Syrup with Novo's Immobilized Glucose Isomerase, Sweetzyme Type Q. 56 pp. Novo Allé, D.K-2880 Bagsvaerd, Denmark; and Novo (1987) Novo Analytical Method No. AF 230/1-GB. Novo method for Activity Determination of the Immobilized Glucose Isomerase-Sweetzyme T. 7 pp. The activity and the stability of the glucose isomerization enzyme control the productivity of the process. The activity of the enzyme is the rate of conversion of glucose to fructose under given process conditions. The stability of the enzyme is an expression of its usable life span and the rate of decay of its activity under process conditions. A third potential, as yet heretofore undemonstrated, would be a change in the equilibrium concentration of fructose obtained under process conditions.

In view of the importance of this process, a need exists for a method by which the effectiveness and efficiency of the process may be improved, particularly in terms of enzyme activity, longevity, process equilibrium and/or flow rate.

SUMMARY OF THE INVENTION

Accordingly, it is an object of the present invention to provide a method for producing high fructose corn syrup from glucose containing syrup, with an improved efficiency.

Further, it is an object of the present invention to provide a glucose containing syrup from dextrin using noble gases with an improved efficiency.

It is also an object of the present invention to provide a process for producing dextrin from starch using noble gases with an improved efficiency.

It is, moreover, an object of the present invention to provide a process for producing high fructose corn syrup from corn starch using noble gases with an improved efficiency.

The above objects and others which will become more apparent in view of the following disclosure are provided by a process for producing high fructose corn syrup from glucose containing syrup, entailing providing glucose containing syrup, from dextrin (and. dextrins from cornstarch) through an enzymatic reaction and isomerizing the syrup through an enzymatic reaction to make high fructose corn syrup, wherein the enzymatic reaction occurs in a gas containing solution which contains at least one gas selected from the group consisting of noble gases.

Broadly speaking, the above objects are provided by a process for producing high fructose corn syrup comprising at least one gas selected from the group consisting of noble gases.

BRIEF DESCRIPTION OF THE DRAWINGS

FIG. 1 represents a diagram of the conventional five stage process for the production of refined fructose from corn starch.

FIG. 2 represents a diagram of the conventional HFCS purification scheme in conjunction with the saccharification and isomerization steps.

FIG. 3 illustrates the relative effects of the gases air, nitrogen, krypton, argon and xenon on the reaction of α-amylase and 4-nitrophenyl-α-D-maltopentaoside (α-PNPG5) at 60° C.

FIG. 4 illustrates the relative effects of the gases air, nitrogen, krypton, argon and xenon on the reaction of amyloglucosidase/4-nitrophenyl-α-D-maltotrioside (α-PNPG3)/α-glucosidase at 37° C.

FIG. 5 illustrates the relative effects of the gases air, nitrogen, krypton, argon and xenon on the reaction of α-amylase/PNPG7/PNPG3/glucoamylase/PNPG1/α-glucosidase at 37° C.

FIG. 6 illustrates the relative effects of the gases air, nitrogen, krypton, argon and xenon on the reaction of α-amylase/amyloglucosidase at 55° C.

FIG. 7 illustrates the results obtained in arithmetic average of % conversion from six vials each of glucose to fructose in a HFCS pilot module using the gases neon, argon, krypton, nitrogen or xenon as a function of time.

FIG. 8 illustrates the profile of % conversion from the average of five vials each.

FIG. 9 illustrates a curve overlay for pot run results using the gases krypton, argon, neon, nitrogen and air.

FIG. 10 illustrates the flow rates for two columns under six treatments. Flow rate measurements were made at each point of sampling. Flow rates were slightly accelerated by argon and neon.

FIG. 11 illustrates the difference in conversion (activity+ flow rate difference) obtained under Ne, Ar and $N_2$ for the conversion of glucose to fructose, at the lower flow rate. Argon gives highest conversion and neon gives a significant but lesser environment over nitrogen.

FIG. 12 illustrates the same differences at the higher flow rate.

FIG. 13 illustrates a comparison of fructose to glucose conversion with glucose to fructose conversion over a 100 hr. run.

FIG. 14 illustrates the effect of temperature on glucose to fructose conversion.

FIG. 15 illustrates the averages for each gas of fructose to glucose conversions and glucose to fructose conversions, and conforms the improvement using neon and argon.

FIG. 16 illustrates the differences between the fructose to glucose conversion and the opposite reaction for each gas.

FIG. 17 illustrates data obtained from other column in another experimental series.

DETAILED DESCRIPTION OF THE PREFERRED EMBODIMENTS

In accordance with the present invention, it has been surprisingly discovered that the industrial process for the enzymatic production of high fructose corn syrup from corn is dramatically improved by the addition of noble gases to the process such that the gases contact the enzymes of the process. Generally, as used herein, the term "noble gases" means argon, neon, krypton, xenon and helium used by themselves or in combination with each other or with other gases as will be described hereinbelow.

Furthermore, the enzymes for which enhanced activity has been demonstrated in accordance with the present invention are, for example, α- and β-amylase, amyloglucosidase, glucose isomerase, pullulanase, limit dextrinase, amylopectinase-6glucohydrolase, mannose isomerase, α- and β-glucosidase and other isomerases and hydrolases.

Examples of other hydrolases include esterases, phosphatases, glycosidases and peptidases, for example.

Specific examples of other hydrolases are, for example, dihydrocoumarin hydrolase, β-D-glucosidase, ribosohomocysteinase, acylmuramylalanine carboxypeptidase, ureidosuccinase, phloretin hydrolase and α-haloacid dehalogenase.

Examples of other isomerases include racemases, epimerases, cis-trans isomerases, intramolecular oxidoreductases and intramolecular transferases, for example.

Specific examples of other isomerases are glucose phosphate isomerase, UDP arabinose 4-epimerase, maleyl acetoacetate isomerase, chorismate mutase and muconate cycloisomerase, for example.

Generally, the noble gases helium, neon, argon, krypton and xenon may be used alone, in admixture with each other or with other gases to enhance the enzymatic activity of amylase, amyloglucosidase and glucose isomerase in the enzymatic production of high fructose corn syrup from corn. Radon is not used as it is a dangerously radioactive gas. Although helium is effective, it is not preferred for use due to its low solubility and tendency to escape during the analysis of reactions.

In accordance with the present invention, the demonstration of enhancement is generally made using conventional apparati, such as isolated colorimetric biochemical enzyme reaction systems, and isolated modular components of the HFCS production process at the laboratory scale.

Generally, enzymatic reaction enhancement may be effected at a range of pressures from about near-vacuum to about 100 atmospheres. However, it is generally preferred that a pressure be used between about 0.001 to about 3 atmospheres. Further, a range of temperature may be used from about near 0 to about 120° C. However, it is generally preferred that a temperature be used in the range of about 40° C. to about 104° C.

The operable and preferred enzyme concentrations which are used for any particular enzymatic reaction in accordance with the present invention are within the knowledge and skill of the artisan. For example, such information may be obtained and/or determined from the literature described above in the Description of the Background.

In accordance with the present invention, any of the noble gases described above may be used alone or in combination with each other or in mixtures with nitrogen, and/or with other common gases such as air, and/or hydrogen and/or nitrous oxide and/or carbon dioxide and/or oxygen. It is noted however that while oxygen may be used, it generally is not used with glucose isomerase reaction systems as oxygen is an inhibitor to glucose isomerase.

In accordance with the present invention, it has been discovered that effective enhancement occurs with gases even in the impure state. Hence, source gases from gas production plants which are not completely purified may advantageously be used.

Additionally, effective enzymatic reaction enhancement is demonstrated across the entire working pH range of the enzymes tested. Moreover, the enzymes may be used either in solution, in bound, in immobilized or in whole cell form.

Moreover, in accordance with the present invention, enzymatic reaction enhancement is demonstrated for each of the enzymes tested at a range of substrate flow and contact rates from conditions of complete substrate limitation to conditions of complete substrate saturation. Further, the thermostability of the enzymes tested has been demonstrated to be altered and sometimes improved by contact with noble gases depending upon temperature and other reaction conditions.

Additionally, effective enzymatic reaction enhancement has been demonstrated across the entire range of reaction conditions which are typically encountered in a modern commercial high fructose corn syrup (HFCS) production process plant, including the full range of enzyme concentrations typically used for such reactions.

Generally, in accordance with the present invention, enzymatic reaction enhancements measured in terms of either rate of yield or stability parameters, and are relative to reactions conducted in air or with no added gases, or to reactions run with added nitrogen, or to a combination of the above. Depending upon the relative controls, enhancements of rate between about 0 and 20% and yield enhancements of about 0 to 5% for glucose isomerase have been obtained.

In general, rate enhancements are obtained from about 2 to 8% real and 5 to 13% relative. Specifically, α-amylase is rate enhanced from about 0 to 35%, with about 3 to 5% being typical under pilot plant conditions.

Amyloglucosidase is enhanced up to about 225% relative under certain conditions in coupled reactions, but under pilot conditions the enhancement is generally slightly less than for amylase.

Yield enhancement is noted for all three enzymes as being up to about 20%. Yield enhancements in the pilot plant are generally small, but significant, being up to about 5%.

As indicated above, the present invention may be effected using any one of argon, neon, krypton, xenon and helium either alone or in combination with each other. As such, any relative mix of these gases may be used, i.e., each gas may be used in the amount of from 0 to 100 volume % or at any value in between. For example, it is advantageous to use inexpensive production plant offstream gases having a composition of about 90% Kr and 10% Xe, in volume %, based on the total gas volume.

However, mixtures of one or more of the noble gases with other gases, such as nitrogen, and/or hydrogen, and/or oxygen, and/or nitrous oxide and/or carbon dioxide may be used. In such mixtures, the one or more noble gases may constitute from greater than 0 to just under 100 volume %. For example, a volume % of from 0.001 to 99.999 may be used. However, any value in between may be used.

In accordance with the present invention, it has been discovered that the gases and gas mixtures of the present invention can effect both thermodynamic and kinetic enhancement of the activities of the specified enzymes. Thus, both the rate and yield of reactions using these enzymes can be enhanced.

Generally, for amylase and amylyoglucoside the following order of enhancing effect is generally observed with the various noble gases:

Xe>Ar>Ne>Kr>He.

For glucose isomerase, the following order of enhancing effect is generally observed with the various noble gases:

Ne>Ar>Kr>Xe>He.

In accordance with the present invention, however, it is partially advantageous if a mixture of about 90 volume % Kr and 10 volume % Xe is used as it is a source of stream gas. It is also preferred that a mixture of about 40 volume % Ne, 10–12 volume % He, 40–50 volume % $N_2$ and 1–2 volume % $H_2$ be used.

However, the gas or gases used may be one or more of the noble gases, i.e., alone or in a mixture with each other, or a mixture of at least one noble gas with nitrogen and/or hydrogen and/or carbon dioxide and/or nitrous oxide and/or $O_2$, except where these latter mixing gases effect the enzymes. Thus, mixtures of any number of the noble gases with any number of the gases nitrogen, and/or hydrogen, and/or carbon dioxide, and/or nitrous oxide and/or oxygen may be used, except that oxygen cannot be used with glucose isomerase.

Thus, the present invention provides a process for producing high fructose corn syrup from glucose containing syrup, which entails isomerizing the glucose containing syrup through an fructose corn syrup, wherein the enzymatic reaction occurs in a gas containing solution which contains at least one gas selected from the group consisting of noble gas.

Preferably, the enzyme used is glucose isomerase. The general and preferred temperature and pressure conditions described above also apply specifically to this aspect of the present invention.

The present invention also provides a process for producing a glucose containing syrup from dextrin, which entails transforming dextrin feedstock to a saccharified syrup through an enzymatic reaction to make glucose containing syrup, wherein the enzymatic reaction occurs in a gas containing solution which contains at least one gas selected from the group consisting of noble gases.

Preferably, the enzyme used is amyloglucosidase. The general and preferred temperature and pressure conditions described above also apply specifically to this aspect of the present invention.

The present invention further provides a method for producing dextrin from starch, which entails transforming starch to dextrin by an enzymatic reaction, wherein the enzymatic reaction occurs in a gas containing solution which contains at least one gas selected from the group consisting of noble gases.

Additionally, the present invention provides a process for producing high fructose corn syrup which entails: a) converting starch to dextrose feed stock through a first enzymatic reaction, b) transforming dextrose feed stock into a saccharified syrup of high quality dextrose feed stock through a second enzymatic reaction and c) isomerizing the saccharified syrup into fructose through a third enzymatic reaction to provide the high fructose corn syrup, wherein at least one of the enzymatic reactions occurs at least partially in a gas containing solution which contains at least one gas selected from the group consisting of noble gases.

Further, in accordance with the present invention the gas containing solution used for the various enzymatic reactions may also contain one or more carrier gas used in admixture with the one or more noble gases. For example, carrier gases such as oxygen, nitrogen, carbon dioxide, nitrous oxide, hydrogen and helium may be noted. However, two points should be emphasized.

First, while helium may be used as a "noble gas" in accordance with the present invention, it may also be used as a "carrier gas" for other "noble gases". That is, it may be used both as a noble gas and a carrier gas.

Second, oxygen is generally not used, as noted above, with glucose isomerase reaction systems as oxygen is an inhibitor to glucose isomerase.

The general principle and description of the interaction between noble gases and enzymes has been disclosed in U.S. Ser. No. 07/706,587 filed Jun. 2, 1991, which is incorporated herein by reference in the entirety.

Having described the above, the present invention will now be further demonstrated by reference to certain examples which are provided solely for purposes of illustration and are not intended to be limitative.

EXAMPLE 1

Purpose: To demonstrate the relative effects of Air, $N_2$, Ar, Kr and Xe on α-Amylase/α-PNPG5 reaction at 60° C. using one substrate concentration. α-PNPG5 is 4-nitrophenyl-α-D-maltopentaoside.

Enzyme:

α-Amylase A-3403, EC 3.2. 1.1 Type XII-A Bacterial from *Bacillus licheniformis*

Unit Definition: One unit will liberate 1.0 mg of maltose from starch in 3 min at pH 6.9 at 20° C.

Aqueous solution containing approx. 15.% sodium chloride 30 mg prot./ml 1000 units/mg prot.

Lot#117-FO850

Substrate:

4-Nitrophenyl-α-D-maltopentaoside (α-PNPG5) Boehringer Mannheim 720496 Lot 11378826-11

Solution Preparation:

Soln A: 0.02 M Sodium Phosphate buffer, pH 6.8 at 25° C. Dissolve 1.39 g $Na_2HPO_4$ and 1.22 g $NAH_2PO_4$ in 2 Liters of DI $H_2O$. Adjust pH to 6.8. pH tested: 6.9 at 25° C.

Soln B: 50 nTwl/L NaCl in 0.02M Sodium phosphate buffer (Soln A) Dissolve 2.92 g NaCl in 1 Liter of 0.02M Sodium phosphate buffer, pH 6.8 (Soln A).

Soln C1: α-Amylase A-3403 (300 units/ml) Dilute 1 ml A-3403 to 100 ml with DI H20.

Soln C2: α-Amylase A-3403 (89.5 units/ml) Dilute 29.8 ml Soln C1 to 100 ml with DI $H_2O$.

Soln D: 4-Nitrophenyl-α-D-maltopentaoside Dilute 62 mg of α-PNPG5 to 65 ml with Soln 8

Parameters:

Gaseous atmospheres:
  * 5 different gaseous atmospheres:
    G1 Air
    G2 Nitrogen
    G3 Argon
    G4 Krypton
    G5 Xenon Temperature:
  * 1 temperature:
    TI 60° C.

Blank:
  R=2 mL Soln D+0.5 mL DI $H_2O$

Spectrophotometric study at 60° C.:

Sample Preparation and runs schedule:
  use blue silicone
  label silicone-sealed cuvettes
  Fill the cuvettes with 2.0 ml of Soln D with a I cc syringe.
  Fill 5 serum vials with 5.0 ml of Soln C2. Stopper and crimp to effect a gas tight system.
  Keep cuvettes and serum vials stoppered when they are not being gassed by leaving 2 10cc syringes filled with the appropriate gas inserted in the cuvette or vial.

MATERIALS NEEDED:

| Cuvettes with blue silicone: | 5 (G × T) |
| --- | --- |
| | 1 (blk) |
| | 6 cuvettes tot. |
| Serum vials (10 cc): | 5 (w/ 5 ml SoLn E) |
| Needles: | B-D 20G1 1/2 |
| Param: | Abs |
| | Slit 1 nm |
| | Speed 1500 nm/min |
| | ASave Y |
| | APrint N |

Background correction: 900–190 nm
CPRG, 400 mn, 60 pts, 16 s. int., 5 cells

Bubble 10×10 cc of the appropriate gas in RIG1 . . . 5 cuvettes. Refrigerate under two 10 cc syringes. Keep refrigerated at least 15 minutes before running.

Bubble 10×10 cc of the appropriate gas in GI . . . 5 serum vials. Refrigerate under two 10 cc syringes.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove G1 . . . 5 serum vials from fridge. Sample Soln C2 (89.5 Units/ml) with 1 cc syringes previously filled with the appropriate gas. Slide the syringes/needle through the silicone but not into the liquid layer, simultaneously push plungers into the liquid and push the plungers simultaneously, run timedrives.

| ([G1, G2, G3, G4, G5], 6OE2R1) | 15 min |
| --- | --- |
| Files: | |
| 6OE2RIGI . . . 5.SP | |
| 5 Files total | |

EXAMPLE 2

Purpose:

To demonstrate the relative effects of Air, $N_2$, Ar, Kr and Xe on Amyloglucosidase/α-PNPG3/α-Glucosidase reaction using one substrate concentration. α-PNPG3 is 4-nitrophenyl-α-D-maltotrioside.

Enzyme:

Amyloglucosidase A-7420 EC 3.2.1.3 from *Aspergillus niger*

Unit Definition: One unit will liberate 1.0 mg of glucose from starch in 3.0 min at pH 4.0 at 55° C.

51 units/mg solid Lot 67 F8690 α-Glucosidase G-8889

Type VII from Yeast

Soln in 50 % glycerol containing bovine serum albumin
  Unit Definition: One unit will liberate 1.0 μmole of D-glucose from α-Nitrophenyl-a-D-glucoside per min at pH 6.8 at 37° C. Using maltose as substrate, one unit will convert 1.0 μmole of maltose to 2.0 μmole of D-glucose per min at pH 6.0 at 25° C.

5 mg prot./ml 75 units/mg prot.

Lot 64 F-02701

Substrate:

4-Nitrophenyl-α-D-maltotrioside (α-PNPG3) Boehringer Mannheim 724777 Lot 12245520-17

Solution preparation:

Soln A: 0.02 M Sodium phosphate buffer, pH 6.8 at 25° C. Dissolve 1.39 g $Na_2 HPO_4$ and 1.22 g $NaH_2 PO_4$ in 2 Liters of DI $H_2O$. Adjust pH to 6.8. pH tested: 6.9 at 25° C.

Soln B: 50 μmol/L NaCl in 0.02 M Sodium phosphate buffer (Soln A) Dissolve 2.92 1 NaCl in 1 Liter of 0.02M Sodium phosphate buffer, pH 6.8 (Soln A .

Soln C: 0.5 nTwl/L α-PNPG3 in Soln B (50 μmol/L NaCl) Dissolve 40 mg α-PNPG3 in 128 ml Soln B Soln D: Amyloglucosidase A-7420 (20.4 u/ml)/α-Glucosidase G-8889 (0. 1875 U/ml ) Dissolve 10 mg of A-7420 in 25 ml Soln A. Add 50 μL of G-8889. Invert to mix.

Parameters:

Gaseous atmospheres:
  * 5 different gaseous atmospheres:
    G1 Air
    G2 Nitrogen
    G3 Argon
    G4 Krypton
    G5 Xenon Temperature:
  * 1 temperature:
    T1 37° C.

Blank:
  R=2 mL Soln C+0.5 mL Soln A

Spectrophotometric study at 37° C.:

Sample Preparation and runs schedule:

use blue silicone label silicone-sealed cuvettes

Fill the cuvettes with 2.0 ml of Soln C with a 1 cc syringe.

Fill 5 serum vials with 5.0 ml of Soln D. Stopper and crimp to effect a gas tight system.

Keep cuvettes and serum vials stoppered when they are not being gassed by leaving 2 10 cc syringes filled with the appropriate gas inserted in the cuvette or vial.

Materials needed:

| | |
|---|---|
| Cuvettes with blue silicone: | 5 (G × T) |
| | 1 (blk) |
| | 6 cuvettes tot. |
| Serum vials (10 cc): | 5 (w/ 5 ml SoLn O) |
| Needles: | B-D 20G1 1/2 |
| Param: | Abs |
| | Slit 1 nm |
| | Speed 1500 nm/min |
| | ASave Y |
| | APrint N |

Background correction: 900–190 nm
CPRG, 400 mn, 80 pts, 16 s. int., 5 cells

Bubble 10×10 cc of the appropriate gas in RIGI..5 cuvettes. Refrigerate under two 10 cc syringes. Keep refrigerated at least 15 minutes before running.

Bubble 10×10 cc of the appropriate gas in GI . . . 5 serum vials. Refrigerate under two 10 cc syringes.

Remove the cuvettes from the refrigerator and remove the syringes/needles from the cuvettes. Tap cuvettes to eliminate bubbles. Wipe walls. Put cuvettes in cell holder. Allow cuvettes to come to temperature.

Remove GI . . . 5 serum vials from fridge. Sample Soln D with 1 cc syringes previously filled with the appropriate gas. Slide the syringes/needle through the silicone but not into the liquid layer, simultaneously push plungers into the liquid and push the plungers simultaneously, run timedrives.

| | |
|---|---|
| ([G1, G2, G3, G4, G5], 37C3R2) | 20 min |
| Files: | |
| 37C3RlGl . . . 5.SP | |
| 37C3RlGl . . . 5.SP | |
| 10 Files total | |

EXAMPLE 3

Purpose:

To demonstrate the relative effects of Air, Ne, Ar, Kr, Xe, $O_2$, $N_2$, 90% Kr/10% Xe, and on α-Amylase/PNPG7/PNPG3/GlucoamylaseTPNP1/ α-Glucosidase reaction at 35° C. using one substrate concentration. PNPG7 is p-nitrophenyl-α-D-maltoheptaoside.

Enzyme:

α-Amylase A-6380 (1.4 -α-D-Glucan-glucanohydrolase; EC 3.2.1.1 ) Unit Definition: One unit will liberate 1.0 mg of maltose from starch in 3 min at pE 6.9 at 20° C.

Type II-A

From Bacillus species 4 x crystallized, lyophilized

2540 Units/mg protein

2080 Units/mg solid (100 mg solid)

Lot#118 F-0150

SIGMA Diagnostic Kit 576-3 (Procedure No. 576 )

Substrate (and kit related enzymes)=α-Amylase reagent

When reconstituted with 3.5 mL D.I.$H_2O$ per vial, contains approximately:

| | |
|---|---|
| PNPG7 | 0.5 μmol/L |
| Sodium chloride | 50 μmol/L |
| Calcium chloride | 5 μmol/L |
| α-Glucosidase (Yeast) | 25,000 U/L |
| Glucoamylase ([Aspergillus niger) | 10,000 U/L |
| Buffer | pH 6.9 ± 1 |

Nonreactive stabilizers and fillers Lot#98 F-6195

Diluents:

Deionized $H_2O$ 0.02M Sodium Phosphate Buffer (pH 7.0 at 25° C. containing 0.05M Sodium Chloride Protocol was determined according to results obtained an May 24, 1990 and May 25, 1990 (see file AMYL3.WP on Disk AMYL1).

Results obtained on May 31, 1990 at t=35° C. were unexpected. The absorbance did not change as theorized therefore t=35° C. will be repeated to verify results obtained on May 31, 1990.

Principle:

The enzymatic reactions involved in the α-amylase assay are as follows:

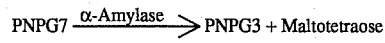

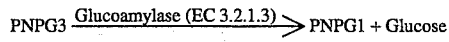

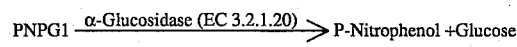

p-Nitrophenol absorbs light at 405 nm and the rate of increase in absorbance at 405 nm is directly proportional to α-Amylase activity. PNPG1 is 4 -nitrophenylglycoside.

Kit Calibration Procedure:

Total volume in covet: 1.025 mL
   25 μL α-Amylase solution with a linearity top limit of 2,000 U/L
   1 mL Amylase Reagent Enzyme/Substrate content per cuvet:
   α-Amylase (Linearity top limit): 0.05 Units

| Amylase Reagent: | |
|---|---|
| PNPG7 | 0.5 μmol |
| Sodium chloride | 50 μmol |
| Calcium chloride | 5 μmol |
| α-Glucosidase (Yeast) | 25 Units |
| Glucoamylase (Aspergillus niger) | 10 Units |

Enzyme/Substrate concentrations in cuvet ($C_{tot}$=1.025 mL):
   α-Amylase (Linearity top limit): 0 V.5%1;8 Units/mL

| Amylase Reagent: | |
|---|---|
| PNPG7 | 0.488 μmol/ml |
| Sodium chloride | 48.8 μmol/ml |
| Calcium chloride | 4.88 μmol/ml |
| α-Glucosidase (Yeast) | 24.4 U/mL |

Parameters:

Gaseous atmospheres:
   * 9 different gaseous atmospheres:

G1 Air (G8)
G2 90% Kr/10% Xe
G3 Argon
G4 Krypton
G5 Xenon
G6 Oxygen $O_2$
G7 Nitrogen $N_2$
G8 Air
G9 Ne
G0 $SF_6$ Temperature:
 * 1 temperature:
   T1 35° C.

Substrate concentration:
 * See solution preparation.
 * 1 substrate concentration:

| α-Amylase A-6380 Reagent A6/100 (12.48 U/mL) (mL) | Amylase reagent Reagent B (mL) |
|---|---|
| 0.5 | 2 |

Blank:
 P8=2 mL Reagent B+0.5 mL 0.02M Na phosphate buffer The same blank is used throughout the experiment.

Enzyme/Substrate content per covet:
 α-Amylase (Linearity top limit): 6.24 Units

| Amylase Reagent: | |
|---|---|
| PNPG7 | 0.78 μmol |
| Sodium chloride | 77.98 μmol |
| Calcium chloride | 7.78 μmol |
| α-Glucosidase (Yeast) | 38.39 Units |
| Glucoamylase (*Aspergillus niger*) | 15.56 Units |

Enzyme/Substrate concentrations in covet ($V_{tot}$=2.5 mL):
 α-Amylase (Linearity top limit): 2,496 Units

| Amylase Reagent: | |
|---|---|
| PNPG7 | 0.31 μmol/ml |
| Sodium chloride | 31.19 μmol/ml |
| Calcium chloride | 3.1 μmol/ml |
| α-Glucosidase (Yeast) | 15.56 U/ml |
| Glucoamylase (*Aspergillus niger*) | 6.22 U/ml |

Runs:
Slit 1=, speed 1,500=/min, 405=, Asave Y, Aprint N, $Y_{max}$=3.0
1. ([G1, G2, G3, G4, G5], T1, P8) 15 min
2. ([G6, G7, G8, G9, G0], T1, P8) 15 min Solution Preparation:
0.02M Sodium phosphate buffer pH 7.0 at 25° C. containing 0.05M Sodium Chloride:
 2 L Deionized water
 2×141.96×0.2×30.5×1/100=1.730 g $Na_2EPO_4$
 2×119.96×0.2×19.5×1/100=0.935 g $NaH_2PO_4$
 2×58.44×0.05=5.84 g NaCl
(pH meter tested: pH 6.71 at 25° C.; adjunction of NaCl lowers NaPhos. buffer pH from 7.0 to pE 6.71)
 Prepared on May 24, 1990
 Stored in refrigerator (0°–5° C.) in a Nalgene bottle.

Enzyme solution: α-Amylase A-6380
 Jun. 4, 1990: Enzyme solution A6/100 was remade from the mother solution (Reagent A) prepared on May 31, 1990.
 0.0100 g A-6380 in 100 mL 0.02M NaPhos. Buffer Reagent A (208 Units/mi). Prepared on May 31, 1990 Stored in refrigerator (0°–5° C.) in a Nalgene Amber bottle (to protect from strong light).
 10 mL Reagent A diluted to 100 mL with NaPhos. Buffer→Reagent A1/10:20.8 Units/mL. Prepared on Jun. 4, 1990 Stored in refrigerator (0°–5° C.) in a Nalgene Amber bottle (to protect from strong light).
 60 mL Reagent A1/10 (20.8 Units/mi) diluted to 100 mL with 0.02M NaPhos. Buffer→Reagent A6/100: 12.48 Units/mL. Prepared on Jun. 4, 1990 Stored in refrigerator (0°–5° C.) in a Nalgene Amber bottle (to protect from strong light).

Amylase reagent:
 Reconstitution of 5 Amylase Reagent vials with 5.0 mL D.I. $H_2O$/each (instead of the 3.5 ML directed by Sigma procedure No. 576): Reagent B

| PNPG7 | 0.39 μmol/L |
|---|---|
| Sodium chloride | 38.89 μmol/L |
| Calcium chloride | 3.89 μmol/L |
| α-Glucosidase (Yeast) | 19,444 U/L |
| Glucoamylase (*Aspergillus niger*) | 7,778 U/L |
| Buffer | pH 6.9 ± 1 |

Nonreactive stabilizers and fillers
NOTE: Considering the yellowing of α-Amylase reagent over time (observed in AMYL3.WP set of experiments), we decided to reconstitute reagent 5 vials at a time before each temperature run).

Sample Preparation and Runs Schedule:
Label silicone-sealed covets
Purge covets with air (3×10 cc)
Fill 10 cc serum vials with α-Amylase solution A6/100 (12.48 U/mL).
Keep serum vials in refrigerator.
8.30 a.m. warm up the spectrophotometer.

| PARAM: | ABS |  |
|---|---|---|
|  | slit 1 |  |
|  | speed 1,500 =/min |  |
|  | Asave Y |  |
|  | Aprint N |  |
| Background correction: | 900–190 rim |  |
| CPRG | 5 cells |  |
|  | 405 nm |  |
|  | Pts 60 | ==> 15 min RUN |
|  | int 15 |  |
|  | $Y_{min}$ = 0—0 |  |
|  | $Y_{max}$ = 3.0 |  |

Set Digitapcontroller on 35° C. and Fisher circulator on 30° C. and high pump speed).

T1 RUNS (35° C.):
 * Reconstitute 5 vials of α-Amylase reagent with 5 mL D.I. $H_2O$: reagent B.
 * Fill P8TIG?+blank covets with 2 mL of Amylase Reagent B with a 1 cc syringe.
 * Bubble 6×10 cc of the appropriate gas into covets. Put in the fridge (under two 10 cc syringes).
 * 10 min. Remove G1 . . . 5 vials from the fridge. Bubble 8×10 cc, of the appropriate gas. Put back in the fridge (under two 10 cc syringes).

* 10 min. Remove T1G1 . . . 5 covets from fridge. Remove syringes from covets. Tap covets to eliminate bubbles. Wipe walls. Put covets in cell holder.
* 10 min. Remove GI . . . 5 vials from fridge. Sample A6/100 solution (12.48 U/mL) with 1 cc syringes previously filled with the appropriate gas, pick syringes into silicone, push plungers simultaneously, run timedrives:

([G1, G2, G3, G4, G5], T1, P8) 15 min

* 10 min. Remove G6 . . . 0 vials from the fridge. Bubble 8×10 cc of the appropriate gas. Put back in the fridge (under two 10 cc syringes).
* 10 min. Remove T1 G6 . . . 0 covets from fridge. Remove syringes from covets. Tap covets to eliminate bubbles. Wipe walls. Put covets in cell holder.
* 10 min. Remove G6 . . . 0 vials from fridge. Sample A6/100 solution (12.48 U/mL) with 1 cc syringes previously filled with the appropriate gas , pick syringes into silicone, push plungers simultaneously, run timedrives:

([G6, G7, G8, G9, GO], TI, P8)15 min

Materials Needed: Jun. 4, 1990

| Siliconed acrylic covets: | 10 (G × T) |
|---|---|
| | 1 (P8) |
| | 11 covets |

0.02M NaPhos. buffer (0.05M NaCl), pH 6.7 (25° C.): 281 mL

Amylase Reagent solution: 66 mL

α-Amylase solution A6/100 (12.48 U/mL): 50 mL

Serum vials (10 cc): 10 (5 mL/each)

Needles: B–D 20G½

| Spectra Files: |
|---|
| P8T1G1 . . . 5.SP |
| PSTIG6 . . . O.SP |

EXAMPLE 4

Purpose:

To demonstrate the relative effects of noble gases He, Ne, Ar, Kr, Xe, as pure gases or in gas mixtures, on glucose isomerase, which is the enzyme involved in the third enzymatic step of the production of High Fructose Corn Syrup (EFCS).

1. Reaction Principle:

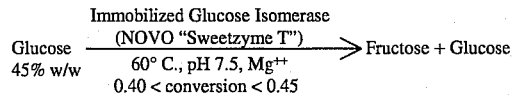

2. Solution Preparation:

a). 0.1% Magnesium Sulfate Solution

Refer to page 2 of the NOVO Analytical Method Number AF 230/1-GE. Dissolve 1-0 9 Of $MgSO_4.7h_2O$ in 700 ml of D.I. $H_2O$. Adjust the pH to 7.5 using 1N NAOH, and di ute to 1000 ml with D.I. $H_2O$.

b). Glucose Substrate Solution

Refer to page 2 of the NOVO Analytical Method Number Af 230/1 GB. The solution is made with 539 g of glucose (anhydrous), 1.0 g of $MgSO_4.7H_2O$, 0.21 g of $NaCO_3$, and 0.18 g of $Na_2S_2O_5$ dissolved in 600 ml of heated (max. 70° C.) and stirred D.I. $H_2O$. After the glucose is dissolved completely in the water, place the solution on a tared balance and add just enough D.I. $H_2O$ to obtain a final solution weight of 1199 g. Place this solution in a sealed container in the refrigerator (0°–5° C.).

3. Vial Preparation:

Two sets of 125 ml serum vials are prepared for each studied gas, one containing the glucose substrate solution (80 ml per vial) and the other one containing Sweetzyme T (5 g dry/vial).

a). Initial Preparation i). Enzyme Vials

For each studied gas, weigh 5 g of dry Sweetzyme T in a 125 ml serum vial. Each vial is numbered and labeled as such to be able to trace any generated data to a particular vial. Add 100 ml of glucose substrate solution to each vial. Seal the vial (rubber stopper+ aluminum seal) and allow the enzyme to soak overnight under refrigeration (0°–5° C.).

Remove aluminum seal and rubber stopper of each vial. Decant the liquid supernatant, being careful not to lose any enzyme particles. Add 100 ml of 0.1% $MgSO_4$ solution to each vial, stopper, and invert several times to mix. Allow the enzyme particles to settle. Decant liquid out. Four additional rinsing with 0–1% $MgSO_4$ solution are done as described above, so that the enzyme is thoroughly rinsed free of the sugar solution. When the rinsing is completed, there is only enough $MgSO_4$ (approx. 15 ml) in each vial to cover the enzyme particles. Keep the vials refrigerated.

For cost purposes, we have decided to recycle the enzyme vials throughout the runs. After each vial run, the enzyme remains in the glucose substrate in its original sealed serum vial, under a positive pressure of nitrogen (10–20 psig). The vials are stored in the refrigerator until the next run. Before a run, on day D-1, the enzyme is rinsed 5 times with $MgSO_4$ solution as described previously.

ii). Substrate Vials

For each studied gas, fill one 125 ml serum vial with 80 ml of Glucose Substrate Solution. Seal the vial (rubber stopper+aluminum seal). Keep refrigerated (0°–5° C.).

b). Purging with Nitrogen

The activity of Sweetzyme T is greatly inhibited by the presence of oxygen, so the vials must be purged with an inert gas before use in the experiment.

i). Enzyme Vials

On day D-1, nitrogen on-line is blown through each vial for 30 min with a delivery pressure of 20 psi.

ii). Substrate Vials

On day D-1, the glucose solution in each vial is bubbled through with nitrogen on-line for 30 min at a delivery pressure of 20 psi.

c). Gassing i). Enzyme Vials

On day D-1, remove the gaseous headspace of each enzyme vial by using a vacuum pump. Refill the vial immediately with twice its headspace (estimated at 100 ml) using the appropriate gas or gas mixture. Gassing is performed at as low of a temperature as possible (around 15° C.), to insure a proper gas saturation at the run temperature 60° C. After this first gassing, the vials are left overnight in the refrigerator (0°–5° C.).

On day D, remove the vials from the refrigerator. Gas vials following the same protocol as described for day D-1. Let vials stand for 30 min.

ii). Substrate Vials

On day D-1, remove the gaseous headspace of each substrate vial by using a vacuum pump. Refill the vial immediately with twice its headspace (estimated at 50 ml) using the appropriate gas or gas mixture. Gassing is performed at as low of a temperature as possible (around 15° C.), to insure a proper gas saturation at the run temperature 60° C. After this first gassing, the vials are left overnight in the refrigerator (0°–5° C.).

On day D, remove the vials from the refrigerator. Gas vials following the same protocol as described for day D-1. Let vials stand for 30 min.

4. Starting the Run:

On day D, place the substrate vials into a shaking water bath (60° C., 140 rpm). Allow them to equilibrate in temperature. For each substrate vial, fill a 60 cc B–D syringe with the appropriate gas or gas mixture and inject it in the vial. Remove the substrate vial from the shaker bath and replace it with the corresponding enzyme vial. Allow the positive pressure in the substrate vial to fill the syringe with glucose solution up to 60 ml. Stopper syringe needle with a septum. Repeat this procedure for each vial. When all the substrate vials have been sampled, inject the content of each syringe (60 ml of gas-saturated glucose solution) into the corresponding enzyme vial. The enzyme vials are injected at 2 minute intervals. The time of the injection determine $t_0$ for each vial.

5. Sampling and Samples Preparation:

a). Sampling Frequency

Samples are taken out of each vial (substrate+enzyme) at 15 minute intervals whenever possible, or 30 minute intervals, or, for longer runs, at 1 hour intervals. Sampling is achieved on a period of 4, 6, or 12 hrs, depending on the vial run experiments. Vials are sampled 2 minutes apart from each other.

b). Sampling Procedure

For each vial, fill a 1 cc B–D syringe with $N_2$. Remove the vial from the shaker bath. Swirl it to allow a good mixing of the sugars. Purge the syringe from the N2 just before puncturing the vial septum. Allow the positive pressure in the vial to fill the syringe with the solution up to 0.55 ml. Try to avoid to a maximum sucking out enzyme particles. Make sure that no particles are clinging to the sides of the vial. Put the vial back into the shaker bath.

c). Preparation of Samples for HPLC Analysis

After stage 2., immediately dilute 0.4 ml of each sample into 50 ml of D.I. $H_2O$. Mix well. Fill a 5 cc B–D syringe with the diluted sample. Fix a syringe filter holder (containing a 0.45 µ nylon filter) at the tip of the syringe. Pass 2 ml of diluted sample through, then fill a 1 ml WATERS HPLC vial with 0.7 ml of diluted sample. Cap the HPLC vial and freeze immediately. Since the samples can be analyzed by HPLC only at a later date following the vial run, it is imperious to freeze the samples to avoid a possible continuation of glucose conversion, caused by any enzyme that could have passed through the filtering operation.

The HPLC vials are labeled according to the following code: TXYGnxy, where XY is the sampling time expressed as the number of 15 min increments, n is the position of the vial in the shaker bath (I<n<9), and xy is the number of the vial run experiment.

6. Sample Analysis:

The respective concentrations of glucose and fructose in the samples are determined by High Pressure Liquid Chromatography.

a). Description of the EIPLC equipment

The following equipment is used:

Waters Automated Gradient Controller

2 Waters 510 HPLC Pumps (A and B)

Waters 712 WISP (Autoinjector)

Waters Temperature Control Module and Column Heater

Waters 991 Photodiode Array Detector

Waters 410 Differential Refractometer

NEC Powermate 2

Software: Waters 990+991 Foreground/Background b). HPLC Analysis Method and Data Filenames i). Column assembly and settings A Sugar-Pak Column (Shodex SC 1011) is used for the glucose/fructose analysis. To protect the column, an in-line filter (0.2 p) and a guard column (Waters C18 Guard Pak) are installed. The column heater is set at 70° C. HPLC grade water (filtered and degassed) is used as the mobile phase at a flow rate of 1 ml/min.

ii). Method

A printout of the data collection method is appended to the present document (Waters 991 method: VR14VER1.SM9).

iii). Filenames

The data files are named according to the following code: TXYGnxyl, where XY is the sampling time expressed as the number of 15 min increments, n is the position of the vial in the shaker bath (1<n<9), and xy is the number of the vial run experiment. 1 means that a single injection is done per HPLC vial.

c). Loading of Samples

Remove the HPLC vials from the freezer. Place them into the WISP carousel. Allow 10 min for thawing. Load the carousel into the WISP.

d). Further Treatment of Data

The data are entered into spreadsheets using LOTUS 123R3 software to generate graphs.

EXAMPLE 5

Purpose:

To demonstrate the relative effects of noble gases Ar, Ne, and Kr as pure gases on α-Amylase and/or Amlyoglucosidase, which are used in the first two steps of the enzymatic process of converting corn starch to High Fructose Corn Syrup. 1. Reaction Principle:

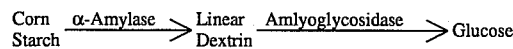

2. Solution Preparation:

a). α-Amylase A-3403 i). Source

Sigma Chemical number A-3403

E.C. 3.2.1.1.

Lot #70 HO298

28 ml, 23.5 mg protein/ml

765 Units/mg protein ii). Preparation 1 ml=17977.5 Units; dilute 10 ml to 100 ml w/deionized $H_2O$; final solution concentration is 1797.75 Units/ml; use 10 ml of this solution per vessel. Prepare fresh before using.

b). Amyloglucosidase A-7420 i). Source

Sigma Chemical number A-7420

E.C. 3.2.1.3
Lot #67 FB690
100 mg, 51 Units/mg solid ii). Preparation 45.7 mg of solid dissolved in 100 ml of OI $H_2O$ (23.3 Units/ml). Use 10.0 ml of this solution per vessel. Prepare fresh before using.

c). 1N $H_2SO_4$

Concentrated sulfuric acid is 36N. 2.8 ml $H_2SO_4$/100 ml DI $H_2O$. Add acid to water, not water to acid. 0.8 ml is needed for each vessel.

d). 1N NaOH 4 g sodium hydroxide pellets per 100 ml DI $H_2O$. 0.8 ml is needed for each vessel.

e). Starch Solution (substrate)

Each vessel is to be filled with 300 g Argo Corn Starch+ 700 ml DI $H_2O$. Mix thoroughly by hand in the reaction vessel immediately before final assembly of each pot. The stirring motor must be used to keep the solution thoroughly mixed from this point forward, beginning less than a minute after hand mixing ends. Set the motor speed control to approximate 100 rpm.

3. Performing the Experiment:

a). Gassing the Mixture ii). Air and Nitrogen Purge

In the vessels that will be saturated with a pure gas or gas mixture other than air, the liquid must be thoroughly purged with nitrogen ($N_2$), for at least an hour. Purge the remainder of the vessels with air for the same time period.

ii). Saturation

Each vessel is pressurized to 20 psi with the appropriate gas, and allowed to mix for 20 minutes. Repeat twice more.

b). The First Enzyme Addition (α-Amylase A-3403)

ii). Syringe Preparation

All injections are performed with new, individually wrapped B–D syringes equipped with 20 gauge 1 ½" needles.

| a. | 1 ml syringe | 0.8 ml NAOH |
| b. | 5 ml syringe | 5.0 ml DI $H_2O$ |
| c. | 10 ml syringe | 10.0 ml α-Amylase solution | ii). Addition Sequence

Once the vessels are opened, they may become contaminated by air and require additional or continuous purging with the saturating gas. After opening the sample ports, they should be kept covered by hand tightening the pressure relief valve over the opening except while actually injecting a solution.

a). Remove the pressure relief valve to provide an injection port that is close enough to the vessel lid to allow the tip of the needle of each injection syringe to reach below the lid and into the vessel cavity.

b). Adjust the pH of the vessel by injecting the 0.8 ml of NaOH from the 1 ml syringe.

c). Rinse the injection port d). Repeat steps a. through c. for each vessel.

e). Inject the enzyme through the injection port from the 10 ml syringe.

f). Rinse the injection port with the remaining DI $H_2O$ from the 5 ml syringe.

g). Replace the pressure relief valve and tighten the fitting securely.

h). Close the sample and pressure release valves and close the gas inlet valve.

i). Repeat steps e. through h. for all the vessels. Allow exactly 2 minutes between the enzyme additions for each vessel.

j). Pressurize each vessel to 20 psi with the appropriate gas, and close all inlet valves immediately after the pressure is reached.

c). Heating the Mixture i). Insulate the pots by covering each cup with several layers of heavy duty aluminum foil. Try to cover as much of the lids as possible without obstructing the operation of the valves or sight of the pressure gauges.

ii). Set the temperature bath controls to 130° C. and insulate the reservoir lids with aluminum foil.

iii). Begin recording times and temperatures for each of the circulating baths and the internal temperatures of the vessels until the vessel temperatures reach 104° C. Try to keep the two temperature baths within 1° C. of each other. Use a stopwatch to keep track of the elapsed time. Keep each vessel pressurized at 20–25 psi.

iv). Hold the vessels at 104° C. for 6 minutes, then begin cooling immediately.

v). Cool the vessels to 90° C. and hold for 2 hours.

vi). Cool the vessels to 60° C., remove the insulation and allow the temperature to stabilize. Make sure each vessel maintains a fairly constant pressure of 20 psi.

vii). Collect the t=0 sample from each vessel according the sampling protocol below (see section E).

d). The Second Enzyme Addition i). Syringe Preparation

| a). | 1 ml syringe | 0.8 ml $H_2SO$ |
| b). | 5 ml syringe | 5.0 ml DI $H_2O$ |
| c). | 10 ml syringe solution | 10.0 ml Amyloglucosidase | ii). Addition Sequence

Once the vessels are opened, they may become contaminated by air and require additional or continuous purging with the saturating gas. After opening the sample ports, they should be kept covered by hand tightening the pressure relief valve over the opening except while actually injecting a solution.

a). Remove the pressure relief valve to provide an injection port that is close enough to the vessel lid to allow the tip of the needle of each injection syringe to reach below the lid and into the vessel cavity.

b). Adjust the pH of the vessel by injecting the 0.8 ml of $H_2SO_4$ from the 1 ml syringe.

c). Rinse the injection port with 1 ml of DI $H_2O$ from the 5 ml syringe, and replace the relief valve and hand tighten until the enzyme is added.

d). Repeat steps a. through c. for each vessel.

e). Inject the enzyme through the injection port from the 10 ml syringe.

f). Rinse the injection port with the remaining DI $H_2O$ from the 5 ml syringe.

g). Replace the pressure relief valve and tighten the fitting securely.

h). Close the sample and pressure release valves and close the gas inlet valve.

i). Repeat steps e. through h. for all the vessels. Allow exactly 2 minutes between the enzyme additions for each vessel.

j). Pressurize each vessel to 20 psi with the appropriate gas, and close all inlet valves immediately after the pressure is reached.

e). Sampling Procedure:

Sample each vessel from left to right (1–6) in two minute intervals in the same order that the enzymes were added. To sample, hold the flexible tube firmly between two fingers, with the end protruding into the sample tube. Carefully open the sample valve and allow the pressure inside the vessel to force 2 ml into the test tube and immediately close the valve. Place the sealed tube in dry ice to freeze immediately. Fill a 60 ml Syringe with the appropriate gas and blow back the sample dip tube to clear it of liquid. The samples were later diluted 1:30 using deionized water before analyzing them on an HPLC system (see below).

f). Sample Analysis:

The glucose concentration in the samples is determined by High Pressure Liquid Chromatography.

i). Description of the HPLC equipment The following equipment is used:

Waters Automated Gradient Controller
2 Waters 510 HPLC Pumps (A and B)
Waters 712 WISP (Autoinjector)
Waters Temperature Control Module and Column Heater
Waters 991 Photodiode Array Detector
Waters 410 Differential Refractometer
NEC Powermate 2
Software: Waters 990+991 Foreground/Background ii). HPLC Analysis Method and Data Filenames a). Column assembly and settings A Sugar-Pak Column (Shodex SC 1011) is used for the glucose analysis. To protect the column, an in-line filter (0.2 μ) and a guard column (Waters C18 Guard Pak) are installed. The column heater is set at 70° C. HPLC grade water (filtered and degassed) is used as the mobile phase at a flow rate of 1 ml/min.

b). Methods

A printout of the data collection method is appended to the present document (Waters 991 method: SUGARPAK1.SM9).

c). Filenames

The HPLC vials are labeled according to the following code: TXY(C,D,E)nxyl, where XY is the sampling time expressed as the number of 15 min increments, (C,D,E) designates the day the sample was taken ("C" is from the first 24 hours, "D" is form the second and "E" is from the third), n is the number of the reaction vessel (1<n<6), xy is the number of the pot run experiment, and 1 means that a single injection is done per HPLC vial.

iii). Loading of Samples

Remove the HPLC vials from the freezer. Place them into the WISP carousel. Allow 10 min for thawing. Load the carousel into the WISP.

iv). Further Treatment of Data

The data are entered into spreadsheets using LOTUS 123R3 software to generate graphs.

EXAMPLE 6

Purpose:

To demonstrate the relative effects of noble gases He, Ne, Ar, Kr, and Xe, as pure gases or in gas mixtures, on the entire HFCS process.

1. Pilot Description:

Pot runs under various gas atmospheres are conducted in the same pot assembly as described in POTPROT.WP. The hydrolyzed starch syrup obtained is then filtered and kept refrigerated until ready for the Glucose Isomerase column runs.

In a second stage, the hydrolyzed starch syrup is pumped, using a peristaltic pump (Micro Tube Pump MP-3), onto a jacketed column (Pharmacia LKB, XK16) containing a 2.51 thick bed of NOVO "Sweetzyme T' in 0.1% $MgSO_4$ solution. The jacket of the column is hooked to a Fisher circulator set at 65° C. The speed of the peristaltic pump is set at 1 to allow a flow giving a conversion of $0.40<x<0.45$. The output flow of the column (High Fructose Corn Syrup) is monitored at regular time intervals using graduated cylinders.

As a reference, a similar run is performed on an identical column, but this time using a 539 g/l glucose solution as the column feed.

2. Solution Preparation:

a). 0.1% Magnesium Sulfate Solution

Refer to page 2 of the NOVO Analytical Method Number AF 230/1-GB. Dissolve 1–0 9 Of $MgSO_4 7H_2O$ in 700 ml of D.I. $H_2O$. Adjust the pH to 7.5 using 1N NAOH, and dilute to 1000 ml with B.I. $H_2O$.

b). Hydrolyzed Starch Syrup

Obtained from the pot run experiments (see POTPROT.WP). Filter and keep refrigerated.

c). Glucose Substrate Solution

Refer to page 2 of the NOVO Analytical Method Number Af 230/1-GB. The solution is made with 539 g of glucose (anhydrous), 1.0 g of $MgSO_4 7H_2O$, 0.21 g of $Na_2CO_3$, and 0.18 g of $Na_2S2O_5$ dissolved in 600 ml of heated (max. 70° C.) and stirred D.I. $H_2O$. After the glucose is dissolved completely in the water, place the solution on a tared balance and add just enough D.I. $H_2O$ to obtain a final solution weight of 1199 g. Place this solution in a sealed container in the refrigerator (0°–5° C.).

3. Column Preparation:

a). Gas Saturation of the Solutions

Fill a stainless steel airtight vessel with 1 L ml of 0.1% $MgSO_2$ solution. Saturate with the appropriate gas or gas mixture. Leave under a 15 psi positive pressure.

Fill a stainless steel airtight vessel with 200 ml of hydrolyzed starch syrup. Saturate with the appropriate gas or gas mixture, Leave under a 15 psi positive pressure.

Fill a stainless steel airtight vessel with 500 ml of glucose substrate solution. Saturate with the appropriate gas or gas mixture. Leave under a 15 psi positive pressure.

b). Gas Saturation of Columns

Hook up, avoiding any air leaks, the vessel containing the $MgSO_4$ solution to both columns. Pump 350 ml of gas-saturated 0.1% $MgSO_4$ solution through each column in order to gas saturate the enzyme beds.

4. Column Runs:

Place the hydrolyzed starch and the glucose solution vessels into a water bath set at 60° C. Allow vessels to equilibrate in temperature. Release positive pressure without allowing any air in. Hook up each vessel to the corresponding column. Pump solutions through columns for 3 hours (pump set at 1). The total volume that has been pumped through each column is recorded at the end of the run.

5. Sampling:

Samples consists of 15 drops of downward flow collected into 3 cc serum vials. The serum vials are stoppered, sealed and frozen immediately. The sampling intervals vary from every 5 min at the beginning of the run, to every 10 min in the middle of the run, to every 15 min by the end of the run.

After proper thawing, filtration, and dilution, the samples are ready for an HPLC analysis using the Sugar-Pak column (see VIALPROT.WP).

6. Column Wash

Between each gas run, the columns are rinsed free of their sugars by pumping 300 ml of D.I. H$_2$O through (pump set at 10) and kept refrigerated to avoid rotting of the enzyme.

Thus, the present invention provides various methods for enhancing each of the enzymatic reactions involved in the HFCS process using the noble gases as defined herein. It also provides a method for enhancing the overall HFCS process using these noble gases.

Further, while the entire HFCS process may be carried out in a single plant in accordance with the present invention, it is specifically contemplated herein that each of the enzymatic reactions involved in the HFCS process may be carried out in separate plants. Hence, the present invention is applicable not only to the overall HFCS process, but also to each enzymatic reaction step involved in that process.

Finally, for more specific information regarding amylase, amyloglucosidase or glucose isomerase reference may be made to Enzymes, by Dixon-Webb, Third Edition (Academic Press)

EXAMPLE 7

A comprehensive experiment was undertaken in order to relate the effects of noble gases upon the important process parameters of temperature, flow rate, enzyme activity and reaction equilibrium. In this experiment, four identical jacketed 1.6×35 cm (70 cc bed volume) columns containing 15 grams dry weight (40 cc bed volume) of the glucose isomerase packing used in the Vial. Runs were prepared according to the protocol outlined above. The columns and substrates were saturated with the gas of interest from a choice of argon, neon, nitrogen, krypton, xenon, helium, or a decile combination of any two or three of these.

One column was run at 0.2 ml/min at 50°, one at 0.2 ml/min at 60°, one at 0.5 ml/min at 50°, and one at 0.5 ml/min at 60°. 1.0 ml samples were collected volumetrically over running times of 4, 8, 12, 24, and 48 hrs. During the first set of experiments, glucose feedstock (as prepared above) was used. During the second set, fructose feedstock of identical concentration was used to analyze the reverse reaction.

Data collected included flow rate, % glucose, % fructose, quantitative evaluation of fructose and glucose, dry solids, temperature, and residual gases.

Comparison of the data for each combination of experiments allows the determination of the effect of the gas, the temperature, the flow rate, the enzyme activity, and the reaction equilibrium. These are each determined independently, then the contribution of each parameter to the others can be calculated. For instance, elevating the temperature increases the flow rate, while lowering temperature and increasing the flow rate maximizes gas effects.

Examples of data produced during these experiments are given in FIGS. 10–17.

FIG. 10 shows the flow rates for two columns under six treatments. Flow rate measurements were made at each point of sampling. Flow rates were slightly accelerated by argon and neon.

FIG. 11 shows the difference in conversion (activity+flow rate difference) obtained under Ne, Ar and N$_2$ for the conversion of glucose to fructose, at the lower flow rate. Argon gives highest conversion and neon gives a significant but lesser enhancement over nitrogen.

FIG. 12 shows the same differences at the higher flow rate. Note that the order of gases in effecting improvement is the same.

FIG. 13 compares fructose to glucose conversion with glucose to fructose conversion over a 100 hr run. The intersections of the two feedstocks for a given gas is the point of equilibrium. Neon and argon saturated columns reach equilibrium before nitrogen saturated columns.

FIG. 14 compares the effect of temperature on glucose to fructose conversion. The columns run at higher temperatures reach equilibria faster.

FIG. 15 depicts the averages for each gas of fructose to glucose conversions and glucose to fructose conversions, and confirm the improvement given by neon and argon.

FIG. 16 depicts the differences between the fructose to glucose conversion and the opposite reaction for each gas, showing that the extent of each effect is related to the differential enhancement of forward vs. reverse reaction rates.

FIG. 17 shows the data obtained from another column in another experimental series. Many replicates from several experimental series confirm our results.

These results clearly show that noble gases enhance the HFCS conversion process at the glucose isomerase step by increasing enzyme activity largely by rate improvement, but also by shifting equilibria. It is also found that noble gases increase flow rates independent of temperature. Noble gases therefore increase the amount of control an operator has over the HFCS conversion process by expanding the working range of enzyme activities, rates and equilibria, and column flow rates. These in turn allow greater ranges in allowable temperature variation and flow characteristics, affecting enzyme longevity.

Having described the present invention, it will be apparent to one of ordinary skill in the art that many changes and modifications can be made to the above-described embodiment without departing from the spirit and scope of the present invention.

What is claimed as new and desired to be secured by Letters Patent of the United States is:

1. A process for producing high fructose corn syrup from glucose containing syrup, comprising isomerizing said glucose containing syrup through an enzymatic reaction to make high fructose corn syrup, wherein said enzymatic reaction occurs in a noble gas-containing solution, at a temperature of about 0° to 50° C.;

said noble gas being selected from the group consisting of argon, xenon, krypton, neon and mixtures thereof, and being present in an amount effective to improve efficiency of the process.

2. The process of claim 1, wherein the enzyme comprises glucose isomerase.

3. The process of claim 1, wherein said process is effected at a temperature in the range of from about near vacuum to about 100 atmospheres.

4. The process of claim 3, wherein said process is effected at a pressure in the range of from about 0.001 to about 3 atmospheres.

5. The process of claim 1, wherein said solution contains a gas which comprises about 90 volume % Kr and 10 volume % Xe.

6. A process for producing high fructose corn syrup, comprising:

a) converting starch to dextrose feed stock through a first enzymatic reaction, b) transforming said dextrose feed stock into a saccharified syrup of high quality dextrose feed stock through a second enzymatic reaction, and c) isomerizing said saccharified syrup into fructose through a third enzymatic reaction to provide said high fructose corn syrup, wherein at least one of the enzymatic reactions occurs in a noble gas-containing solution at a temperature of from about 0° to 50° C.;

said noble gas being selected from the group consisting of argon, xenon, krypton, neon and mixtures thereof, and being present in an amount effective to improve efficiency of the process.

7. The process of claim 6, wherein said first and second enzymatic reactions utilize amylase, amyloglucosadase or a mixture thereof.

8. The process of claim 6, wherein said third enzymatic reaction utilizes glucose isomerase.

9. The process of claim 1, wherein said process is effected at a pressure in a range of from about near vacuum to 100 atmospheres.

10. The process of claim 9, wherein said process is effected at a pressure in the range of from about 0.001 to about 3 atmospheres.

11. A process of claim 1, wherein the process contains a gas which comprises about 90 volume % Kr and 10 volume % Xe.

* * * * *